(12) United States Patent
Donoghue et al.

(10) Patent No.: US 7,212,851 B2
(45) Date of Patent: May 1, 2007

(54) MICROSTRUCTURED ARRAYS FOR CORTEX INTERACTION AND RELATED METHODS OF MANUFACTURE AND USE

(75) Inventors: John Philip Donoghue, Providence, RI (US); Nicholas George Hatsopoulos, Chicago, IL (US); Sylvain Martel, Newton, MA (US); Timothy A. Fofonoff, Somerville, MA (US); Robert J. Dyer, Duluth, GA (US); Ian W. Hunter, Lincoln, MA (US)

(73) Assignee: Brown University Research Foundation, Providence, RI (US)

( * ) Notice: Subject to any disclaimer, the term of this patent is extended or adjusted under 35 U.S.C. 154(b) by 506 days.

(21) Appl. No.: 10/278,853

(22) Filed: Oct. 24, 2002

(65) Prior Publication Data

US 2004/0082875 A1    Apr. 29, 2004

(51) Int. Cl.
*A61B 5/04* (2006.01)

(52) U.S. Cl. ..................... 600/544; 600/378
(58) Field of Classification Search ............... None
See application file for complete search history.

(56) References Cited

U.S. PATENT DOCUMENTS

| | | | |
|---|---|---|---|
| 3,837,339 A | 9/1974 | Aisenberg et al. | |
| 3,850,161 A | 11/1974 | Liss | |
| 4,055,175 A | 10/1977 | Clemens et al. | |
| 4,146,029 A | 3/1979 | Ellinwood, Jr. | |
| 4,294,245 A | 10/1981 | Bussey | |
| 4,360,031 A | 11/1982 | White | |
| 4,461,304 A | 7/1984 | Kuperstein | |
| 4,633,889 A | 1/1987 | Talalla et al. | |
| 4,690,142 A | 9/1987 | Ross et al. | |
| 4,837,049 A | 6/1989 | Byers et al. | |
| 4,865,048 A | 9/1989 | Eckerson | |
| 4,878,913 A | 11/1989 | Aebischer et al. | |
| 4,883,666 A | 11/1989 | Sabel et al. | |

(Continued)

FOREIGN PATENT DOCUMENTS

WO    WO 01/43635    6/2001

(Continued)

OTHER PUBLICATIONS

International Publication No. WO 03/035165, May 1, 2003, Nicolelis et al.

(Continued)

*Primary Examiner*—Robert L. Nasser
(74) *Attorney, Agent, or Firm*—Finnegan, Henderson, Farabow, Garrett & Dunner, L.L.P.

(57) ABSTRACT

A brain implant system consistent with embodiments of the present invention includes an electrode array having a plurality of electrodes for sensing neuron signals. A method for manufacturing the electrode array includes machining a piece of an electrically conductive substance to create a plurality of electrodes extending from a base member. Each electrode also has a corresponding base section. A nonconductive layer is provided around at least a portion of the base section of each electrode to support the plurality of electrodes. The base section of the electrodes are then cut to separate the base member from the plurality of electrodes supported by the nonconductive support layer. The present invention also includes a complete brain implant system using the above electrode array.

26 Claims, 15 Drawing Sheets

U.S. PATENT DOCUMENTS

| | | | |
|---|---|---|---|
| 4,969,468 A | 11/1990 | Byers et al. | |
| 5,037,376 A | 8/1991 | Richmond et al. | |
| 5,081,990 A | 1/1992 | Deletis | |
| 5,119,832 A | 6/1992 | Xavier | |
| 5,156,844 A | 10/1992 | Aebischer et al. | |
| 5,215,088 A | 6/1993 | Normann et al. | |
| 5,325,865 A | 7/1994 | Beckman et al. | |
| 5,361,760 A | 11/1994 | Normann et al. | |
| 5,423,877 A | 6/1995 | Mackey | |
| 5,445,608 A | 8/1995 | Chen et al. | |
| 5,458,631 A | 10/1995 | Xavier | |
| 5,474,547 A | 12/1995 | Aebischer et al. | |
| 5,617,871 A | 4/1997 | Burrows | |
| 5,638,826 A | 6/1997 | Wolpaw et al. | |
| 5,687,291 A | 11/1997 | Smyth | |
| 5,692,517 A | 12/1997 | Junker | |
| 5,697,951 A | 12/1997 | Harpstead et al. | |
| 5,702,432 A | 12/1997 | Chen et al. | |
| 5,713,923 A | 2/1998 | Ward et al. | |
| 5,735,885 A | 4/1998 | Howard, III et al. | |
| 5,758,651 A | 6/1998 | Nygard et al. | |
| 5,797,898 A | 8/1998 | Santini, Jr. et al. | |
| 5,814,089 A | 9/1998 | Stokes et al. | |
| 5,843,093 A | 12/1998 | Howard, III | |
| 5,843,142 A | 12/1998 | Sultan | |
| 5,855,801 A | 1/1999 | Lin et al. | |
| 5,873,840 A | 2/1999 | Neff | |
| 5,928,228 A | 7/1999 | Kordis et al. | |
| 5,938,688 A | 8/1999 | Schiff | |
| 5,938,689 A | 8/1999 | Fischell et al. | |
| 5,938,690 A | 8/1999 | Law et al. | |
| 6,001,065 A | 12/1999 | DeVito | |
| 6,006,124 A | 12/1999 | Fischell et al. | |
| 6,016,449 A | 1/2000 | Fischell et al. | |
| 6,024,700 A | 2/2000 | Nemirovski et al. | |
| 6,024,702 A | 2/2000 | Iversen | |
| 6,027,456 A | 2/2000 | Feler et al. | |
| 6,038,477 A | 3/2000 | Kayyali | |
| 6,061,593 A | 5/2000 | Fischell et al. | |
| 6,086,582 A | 7/2000 | Altman et al. | |
| 6,091,015 A | 7/2000 | del Valle et al. | |
| 6,092,058 A | 7/2000 | Smyth | |
| 6,094,598 A | 7/2000 | Elsberry et al. | |
| 6,113,553 A | 9/2000 | Chubbuck | |
| 6,125,300 A | 9/2000 | Weijand et al. | |
| 6,128,538 A | 10/2000 | Fischell et al. | |
| 6,134,474 A | 10/2000 | Fischell et al. | |
| 6,154,678 A | 11/2000 | Lauro | |
| 6,161,045 A | 12/2000 | Fischell et al. | |
| 6,163,725 A | 12/2000 | Peckham et al. | |
| 6,169,981 B1 | 1/2001 | Werbos | |
| 6,171,239 B1* | 1/2001 | Humphrey | 600/372 |
| 6,175,762 B1 | 1/2001 | Kirkup et al. | |
| 6,181,965 B1 | 1/2001 | Loeb et al. | |
| 6,185,455 B1 | 2/2001 | Loeb et al. | |
| 6,216,045 B1 | 4/2001 | Black et al. | |
| 6,224,549 B1 | 5/2001 | Drongelen | |
| 6,240,315 B1 | 5/2001 | Mo et al. | |
| 6,254,536 B1 | 7/2001 | DeVito | |
| 6,263,237 B1 | 7/2001 | Rise | |
| 6,280,394 B1 | 8/2001 | Maloney et al. | |
| 6,309,410 B1 | 10/2001 | Kuzma et al. | |
| 6,313,093 B1 | 11/2001 | Frey, II | |
| 6,319,241 B1 | 11/2001 | King et al. | |
| 6,353,754 B1 | 3/2002 | Fischell et al. | |
| 6,354,299 B1 | 3/2002 | Fischell et al. | |
| 6,356,784 B1 | 3/2002 | Lozano et al. | |
| 6,358,202 B1 | 3/2002 | Arent | |
| 6,360,122 B1 | 3/2002 | Fischell et al. | |
| 6,366,813 B1 | 4/2002 | DiLorenzo | |
| 6,427,086 B1 | 7/2002 | Fischell et al. | |
| 6,436,708 B1 | 8/2002 | Leone et al. | |
| 6,459,936 B2 | 10/2002 | Fischell et al. | |
| 6,466,822 B1 | 10/2002 | Pless | |
| 6,473,639 B1 | 10/2002 | Fischell et al. | |
| 6,480,743 B1 | 11/2002 | Kirkpatrick et al. | |
| 6,577,893 B1 | 6/2003 | Besson et al. | |
| 6,620,415 B2 | 9/2003 | Donovan | |
| 6,920,351 B2* | 7/2005 | Mitra et al. | 600/544 |
| 2001/0023368 A1 | 9/2001 | Black et al. | |
| 2001/0027336 A1 | 10/2001 | Gielen et al. | |
| 2001/0029391 A1 | 10/2001 | Gluckman et al. | |
| 2001/0051819 A1 | 12/2001 | Fischell et al. | |
| 2001/0056290 A1 | 12/2001 | Fischell et al. | |
| 2002/0002390 A1 | 1/2002 | Fischell et al. | |
| 2002/0013612 A1 | 1/2002 | Whitehurst | |
| 2002/0016638 A1 | 2/2002 | Mitra et al. | |
| 2002/0077620 A1 | 6/2002 | Sweeney et al. | |
| 2002/0099412 A1 | 7/2002 | Fischell et al. | |
| 2002/0169485 A1 | 11/2002 | Pless et al. | |
| 2003/0004428 A1 | 1/2003 | Pless et al. | |
| 2003/0082507 A1 | 5/2003 | Stypulkowski | |
| 2003/0083716 A1 | 5/2003 | Nicolelis et al. | |
| 2003/0083724 A1 | 5/2003 | Jog et al. | |
| 2003/0093129 A1 | 5/2003 | Nicolelis et al. | |
| 2004/0006264 A1* | 1/2004 | Mojarradi et al. | 600/378 |
| 2004/0138579 A1* | 7/2004 | Deadwyler et al. | 600/544 |

FOREIGN PATENT DOCUMENTS

| | | |
|---|---|---|
| WO | WO 01/60445 | 8/2001 |
| WO | WO 01/93756 A2 | 12/2001 |
| WO | WO 02/093312 A2 | 11/2002 |
| WO | WO 02/100267 A1 | 12/2002 |
| WO | WO 03/061465 A2 | 7/2003 |

OTHER PUBLICATIONS

International Publication No. WO 03/037231, May 8, 2003, Nicolelis et al.

Kensall D. Wise et al., "An Integrated-Circuit Approach to Extracellular Microelectrodes, " IEEE Transactions on Biomedical Engineering, vol. BME-17, No. 3, Jul. 1970, pp. 237-247.

Donald R. Humphrey et al., "Predicting Measures of Motor Performance from Multiple Cortical Spike Trains," Science, New Series, vol. 170, Issue 3959, Nov. 13, 1970, pp. 758-762.

A. Bohg, "Ethylene Diamine-Pyrocatechol-Water Mixture Shows Etching Anomaly in Boron-Doped Silicon," Journal of the Electrochemical Society, vol. 118, No. 2, Feb. 1971, pp. 401-402.

Donald R. Humphrey, "Relating Motor Cortex Spike Trains to Measures of Motor Performance," Department of Physiology, Emory University, Brain Research, No. 40, 1972, pp. 7-18.

Arnold Starr et al., "An Evaluation of Photoengraved Microelectrodes for Extracellular Single-Unit Recording," IEEE Transactions on Biomedical Engineering, vol. BME-20, No. 4, Jul. 1973, pp. 291-293.

Kensall D. Wise et al., "A Low-Capacitance Multielectrode Probe for Use in Extracellular Neurophysiology," IEEE Transactions on Biochemical Engineering, vol. BME-22, No. 3, May 1975, pp. 212-219.

V. B. Mountcastle et al., "Posterior Parietal Association Cortex of the Monkey: Command Functions for Operations Within Extrapersonal Space," The Journal of Neurophysiology, vol. 38, No. 4, 1975, pp. 871-908.

Edward M. Schmidt, "Single Neuron Recording From Motor Cortex as a Possible Source of Signals for Control of External Devices," Annals of Biochemical Engineering, vol. 8, 1980, pp. 339-349.

A. J. S. Summerlee et al., "The effect of behavioural arousal on the activity of hypothalamic neurons in unanaesthetized, freely moving rats and rabbits," Proceedings of the Royal Society of London Series B-Biological Sciences, Jan. 1982, pp. 263-272.

Spencer L. BeMent, et al., "Solid-State Electrodes for Multichannel Multiplexed Intracortical Neuronal Recording," IEEE Transactions on Biomedical Engineering, vol. BME-33, No. 2, Feb. 1986, pp. 230-241.

Apostolos P. Georgopoulos et al., "Neuronal Population Coding of Movement Direction," Science, vol. 233, Sep. 26, 1986, pp. 1416-1419.

Kenneth L. Drake et al., "Perormance of Planar Multisite Microprobes in Recording Extracellular Single-Unit Intracortical Activity," IEEE Transactions on Biomedical Engineering, vol. 35, No. 9, Sep. 1988, pp. 719-732.

Patrick K. Campbell et al., "A chronic intracortical electrode array: Prelimanry results," Journal of Biomed. Material Res.: Applied Biomaterials, vol. 23, No. 2, 1989, pp. 245-259.

Andrew R. Mitz et al., "Learning-dependent Neuronal Activity in the Premotor Cortex: Activity during the Acquisition of Conditional Motor Associations," The Journal of Neuroscience, vol. 11, No. 6, Jun. 1991, pp. 1855-1872.

Patrick K. Campbell et al., "A Silicon-Based, Three-Dimensional Neural Interface: Manufacturing Processes for an Intracortical Electrode Array," IEEE Transactions, 1991, pp. 758-768.

A. C. Hoogerwerf et al., "A Three-Dimensional Neural Recording Array," IEEE Transactions, 1991, pp. 120-123.

Gregory T. A. Kovacs et al., "Regeneration Microelectrode Array for Peripheral Nerve Recording and Stimulation," Transactions on Biomedical Engineering, vol. 39, No. 9, Sep. 1992, pp. 893-902.

Kelly E. Jones et al., "A Glass/Silicon Composite Intracortical Electrode Array," Annals of Biomedical Engineering. vol. 20, 1992, pp. 423-437.

Miguel A. L. Nicolelis et al., "Induction of immediate spatiotemporal changes in thalamic networks by peripheral block of ascending cutaneous information," Letters to Nature, vol. 361, Feb. 11, 1993, pp. 533-536.

Reinhard Eckhorn et al., "A new method for the insertion of multiple microphobes into neural and musclar tissue, including fiber electrodes, fine wires, needles and microsensors," Journal of Neuroscience Methods, vol. 49, Nos. 1/2, 1993, pp. 175-179.

Craig T. Nordhausen et al., "Optimizing recoding capabilities of the Utah Intracortical Electrode Array," Brain Research, vol. 637, Nos. 1/2, Feb. 21, 1994, pp. 27-36.

Jamille F. Hetke et al., "Silicon Ribbon Cables for Chronically Implantable Microelectrode Arrays," IEEE Transactions on Biomedical Engineering, vol. 41, No. 4, Apr. 1994, pp. 314-321.

Miguel A.L. Nicolelis et al., "Spatiotemporal of Structure of Somatosensory Responses of Many-Neuron Ensembles in the Rat Ventral Posterior Medial Nucleus of the Thalmus," The Journal of Neuroscience, vol. 14, No. 6, Jun. 1994, pp. 3511-3532.

Arnold C. Hoogerwerf et al., "A Three-Dimensional Microelectrode Array for Chronic Neural Recording," IEEE Transactions on Biomedical Engineering, vol. 41, No. 12, Dec. 1994, pp. 1136-1146.

Camilo Toro et al., "8-12 Hz rhythmic oscillations in human motor cortex during two-dimensional arm movements: evidence for representation of kinematic parameters," Departments Neurology, Neurosurgery, and Physiology, University of Minnesota; MINCEP Epilepsy Care, P.A.; The Minnesota Epilepsy Group of United and St. Paul Children's Hospital; and Human Motor Control Section, National Institue of Neurological Disorders and Stroke, National Institutes of Health, Electroencephalography and Clinical Neurophysiology, No. 93, 1994, pp. 390-403.

Anthony L. Owens et al., "Multi-electrode array for measuring evoked potentials from surface of ferret primary auditory cortex," Journal of Neuroscience Methods, vol. 58, Nos. 1/2, May 1995, pp. 209-220.

Miguel A. L. Nicolelis et al., "Sensorimotor Encoding by Sychronous Neural Ensemble Activity at Multiple Levels of the Somatosensory System," Science, vol. 268, Jun. 2, 1995, pp. 1353-1358.

Jerome N. Sanes et al., "Shared Neural Substrates Controlling Hand Movements in Human Motor Cortex," Science, vol. 268, Jun. 23, 1995, pp. 1775-1777.

D. M. Halliday et al., "A Framework for the Analysis of Mixed Time Series/Point Process Data-Theory and Application to the Study of Physiological Tremor, Single Motor Unit Discharges and Electromyograms," Progress in Biophysics Molecular Biology, vol. 64, Nos. 2/3, 1995, pp. 237-278.

Qing Bai et al., "High-Yield Process for Three-Dimensional Microelectrodes Arrays," Solid-State Sensor and Actuator Workshop, Hilton Head, South Carolina, Jun. 2-6, 1996, pp. 262-265.

Changhyun Kim et al., "A 64-Site Multishank CMOS Low-Profile Neural Stimulating Probe," IEEE Journal of Solid-State Circuits, vol. 31, No. 9, Sep. 1996, pp. 1230-1238.

Gwo-Ching Chang et al., "Real-time implementation of electromyogram pattern recognition as a control command of man-machine interface," Medical Engineering Phys., vol. 18, No. 7, 1996, pp. 529-537.

P. Nisbet, "Integrating assistive technologies: current practices and future possibilities," Med. Eng. Phys., vol. 18, No. 3, 1996, pp. 193-202.

Miguel A. L. Nicolelis et al., "Reconstructing the Engram: Simultaneous, Multisite, Many Single Neuron Recordings," Neuron, vol. 18, Apr. 1997, pp. 529-537.

TR Scott et al., "The Monitoring of Tendon Tension with an Implantable Intratendon Probe and Its Use in the Control of Neuroprotheses," IEEE Transactions on Rehabilitation Engineering, vol. 5, No. 2, Jun. 1997, pp. 233-235.

Barbara M. Faggin et al., "Immediate and simultaneous sensory reorganization at cortical and subcortical levels of the somatosensory system," Proc. Natl. Acad. Science USA, vol. 94, Aug. 1997, pp. 9428-9433.

Nicolelis, Miguel A.L. "Trigeminal System Plasticity During Facial Anethesia," Department of Health and Human Services, Public Health Service, Grant No. 2 R01 DE11451-05, Including Summary Statement, Oct. 1997.

Robert M. Bradley et al., "Long term chronic recordings from peripheral sensory fibers using a sieve electrode array," Journal of Neuroscience Methods, vol. 73, 1997, pp. 177-186.

David K. Warland et al., "Decoding Visual Information From a Population of Retinal Ganglion Cells," The American Physiological Society, 1997, pp. 2336-2350.

Steven P. Wise et al, "Premotor and Parietal Cortex: Cortiococortical Connectivity and Combinatorial Computations," Annual Review of Neuroscience, vol. 20, 1997, pp. 25-42.

P. R. Kennedy et al., "Restoration of neural output from a paralyzed patient by a direct brain connection," NeuroReport, vol. 9, No. 8, Jun. 1998 pp. 1707-1711.

Paolo Dario et al., "Neural Interfaces for Regenerated Nerve Stimulation and Recording," IEEE Transactions on Rehabilitation Engineering, vol. 6, No. 4, Dec. 1998, pp. 353-363.

Nicholas G. Hatsopoulos et al., "Information about movement direction obtained from synchronous activity of motor cortical neurons," Proc. Natl. Sci. USA, vol. 95, Dec. 1998, pp. 15706-15711.

John P. Donoghue et al., "Neural Discharge and Local Field Potential Oscillations in Primate Motor Cortex During Voluntary Movements,"The American Physiological Society, 1998, pp. 159-173.

Nicolelis, Miguel A. L. "Trigeminal System Plasticity During Facial Anethesia," Department of Health and Human Services, Public Health Service, Grant No. 2 R01 DE 11451-06, Apr. 1999.

Gregor Rainer et al., "Prospective Coding for Objects in Primate Prefontal Cortex," The Journal of Neuroscience, vol. 19, No. 13, Jul. 1, 1999, pp. 5493-5505.

John K. Chapin et al., "Real-time control of a robot arm using simultaneously recorded neurons in the motor cortex,"Department of Neurobiology and Anatomy, Duke University Medical Center, Nature Neuroscience, vol. 2, No. 7, Jul. 1999, pp. 664-670.

E. M. Maynard et al., "Neuronal Interactions Improve Cortical Population Coding of Movement Direction," The Journal of Neuroscience, vol. 19, No. 18, Sep. 15, 1999, pp. 8083-8093.

F. Gandolfo et al., "Cortical correlates of learning in monkeys adapting to a new dynamical environment," PNAS, vol. 97, No. 5, Feb. 29, 2000, pp. 2259-2263.

J. F. Marsden et al., "Organization of Cortical Activities Related to Movement in Humans," The Journal of Neuroscience, vol. 20, No. 6, Mar. 15, 2000, pp. 2307-2314.

D. Gareth Evans et al., "Controlling Mouse Pointer Position Using an Infrared Head-Operated Joystick," IEEE Transactions on Rehabilitation Engineering, vol. 8, No. 1, Mar. 2000, pp. 107-117.

Qing Bai et al., "A High-Yield Microassembly Structure For Three-Dimensional Microelectrode Arrays," IEEE Transactions on Biomedical Engineering, vol. 47, No. 3, Mar. 2000, pp. 281-289.

Nicolelis, Miguel A.L. "Trigeminal System Plasticity During Facial Anethesia," Department of Health and Human Services, Public Health Service, Grant No. 2 R01 DE11451-07, Apr. 2000.

Nicolelis, Miguel A.L., "Corticofugal Modualtion of Tactile Sensory Processing," Department of Health and Human Services, Public Health Service, National Institute of Dental and Craniofacial Research of the Nationsl Institutes of Health, Grant No. 1 R01 DE13810-01 A1, Jun. 2000.

Jonathan R. Wolpaw et al., "Brian-Computer Interface Technology: A Review of the First International Meeting," IEEE Transactions on Rehabilitation Engineering, vol. 8, No. 2, Jun. 2000, pp. 164-173.

Simone P. Levine et al., "A Direct Brain Interface Based on Event-Related Potentials," IEEE Transactions on Rehabilitation Engineering, vol. 8, No. 2, Jun. 2000, pp. 180-185.

Robert E. Issacs et al., "Work Toward Real-Time Control of a Cortical Neural Prothesis," IEEE Transactions on Rehabilitation Engineering, vol. 8, No. 2, Jun. 2000, pp. 196-198.

Scott Makeig et al., A Natural Basis for Efficient Brain-Actuated Control, IEEE Transactions on Rehabilitation Engineering, vol. 8, No. 2, Jun. 2000, pp. 208-211.

Johan Wessberg et al., "Real-time predicton of hand trajectory by ensembles of cortical neurons in primates," Nature, vol. 408, Nov. 16, 2000, pp. 361-365.

Jerome N. Sanes et al., "Plasticity and Primary Motor Cortex," Annual Reviews, Neuroscience, Brown University Library, vol. 23, 2000, pp. 393-415.

Jonathan C. Jarvis et al., "The application and technology of implantable neuromuscular stimulators: an introduction and overview," Medical Engineering & Physics, No. 23, Jan. 11, 2001, pp. 3-7.

Miguel A. L. Nicolelis, "Real-time direct interfaces between the brain and electronic and mechanical devices could one day be used to restore sensory and motor functions lost through injury or disease. Hybrid brain-machine interfaces also have the potential to enhance our perceptual, motor and cognitive capabilities by revolutionizing the way we use computers and interact with remote environments," Nature, vol. 409, Jan. 18, 2001, pp. 403-407.

Gerald E. Loeb et al., "BION™ system for distributed neural prosthetic interfaces," Medical Engineering & Physics, vol. 23, Jan. 26, 2001, pp. 9-18.

Patrick J. Rousche et al., "Flexible Polyimide-Based Intracortical Electrode Arrays with Bioactive Capabilty,"IEEE Transactions on Biomedical Engineering, vol. 48, No. 3, Mar. 2001, pp. 361-371.

Nicolelis, Miguel A.L., "Trigeminal System Plasticity During Facial Anethesia," Department of Health and Human Services, Public Health Service, Grant No. 2 R01 DE11451-08, Apr. 2001.

Qing Bai et al., "Single-Unit Neural Recording with Active Microelectrode Arrays, " IEEE Transactions on Biomedical Engineering, vol. 48, No. 8, Aug. 2001, pp. 911-920.

David L. Zealear et al., "The Biocompatabilty, Integrity, and Positional Stability of an Injectable Microstimulator for Reanimation of the Paralyzed Larynx," IEEE Transactions on Biomedical Engineering, vol. 48, No. 8, Aug. 2001, pp. 890-897.

Dawn M. Taylor et al., "Using Virtual Reality to Test the Feasibility of Controlling an Upper Limb Fes System Directly from Multiunit Activity in the Motor Cortex," Arizona State University; and The Neurosciences Institute, Summer 2001, pp. 1-3.

Ranu Jung et al., "Real-Time Interaction Between a Neuromorphic Electronic Circuit and the Spinal Cord," IEEE Transactions on Neural Systems and Rehabilitation Engineering, vol. 9, No. 3, Sep. 2001, pp. 319-326.

Shay Shoham, "Advances Towards an Implantable Motor Cortical Interface," The University of Utah, Dec. 2001, pp. 1-157.

John K. Chapin et al., "Neural Prosteses for Restoration of Sensory and Motor Function," CRC Press, LLC, 2001, Chapters 6, 8 and 9, pp. 179-219, pp. 235-261, pp. 263-283.

Andrew B. Schwartz et al., "Extraction algorithms for cortical control of arm prosthetics," The Neuroscience Institute; and Department of Bioengineering, Arizona State Univeristy, 2001, pp. 701-707.

István Ulbert et al., "Multiple microelectrode-recording system for human intracortical applications, " Journal of Neuroscience Methods, vol. 106, 2001, pp. 69-79.

Mijail D. Serruya et al., "Instant Neural Control of a Movement Signal," Nature, vol. 416, Mar. 14, 2002, pp. 141-142.

Nicolelis, Miguel A.L. "Corticofugal Modulation of Tactile Sensory Processing," Department of Health and Human Services, Public Health Service, National Institute of Dental and Craniofacial Research of the Nationsl Institutes of Health, Grant No. 5 R01 DE013810-02, Mar. 2002.

Nicolelis, Miguel A.L., "Trigeminal System Plasticity During Facial Anethesia," Department of Health and Human Services, Public Health Service, Grant No. 2 R01 DE11451-09, Apr. 2002.

Dawn M. Taylor et al., "Direct Cortical Control of 3D Neuroprosthetic Devices," Science, vol. 296, Jun. 7, 2002, pp. 1829-1832.

John P. Donoghue, "Connecting cortex to machines: recent advances in brain interfaces," Nature Neuroscience Supplement, vol. 5, Nov. 2002, pp. 1085-1088.

Y. Gao, et al., "Probablistic Inference of Hand Motion from Neural Activity in Motor Cortex," In Advances in Neural Information Processing Systems 14, The MIT Press, 2002, pp. 1-8.

Mijail Serruya et al., "Rubustness of neuroprosthetic decoding algorithms," Biological Cybernetics, 2003, pp. 1-10.

Miguel A. L. Nicolelis, "Brain-machine interfaces to restore motor function and probe neural circuits," Nature Reviews, Neuroscience, vol. 4, May 2003, pp. 417-422.

Frank Wood et al., "On the Variability of Manual Spike Sorting," Brown University, Providence, RI, Jul. 1, 2003, pp. 1-19.

Wei Wu et al., "Modeling and Decoding Motor Cortical Activity using a Switching Kalman Filter," Brown University, Providence, RI, Jul. 1, 2003, pp. 1-30.

Jose M. Carmena et al., "Learning to Controla Brain-Machine for Reaching and Grasping by Primates," PLOS Biology, vol. 1, Issue 2, Oct. 13, 2003, pp. 1-16.

Libet, Benjamin, "Unconscious Cerebral Initative and the Role Conscious Will in Voluntary Action," The Behavorial and Brain Sciences 1995) 8, pp. 529-566.

Norretranders, Tor, "The User Illusion," Penguin Books, 1991, Chapter 12, pp. 310-328.

Mohammad Mojarradi, "A Miniaturized Neuroporosthesis Suitable for Implantation Into the Brain," IEEE Transactions on Neural Systems and Rehabilitation Engineering, vol. 11, no. 1, Mar. 2003.

Morten K. Haugland et al., "Cutaneous Whole Nerve Recordings Used for Correction of Footdrop in Hemiplegic Man," IEEE Transactions on Neural Systems and Rehabilitation Engineering vol. 3, No. 4, Dec. 1995.

Miguel A. L. Nicolelis, "Brain-Machine Interfaces to Restore Motor Function and Probe Neural Circuits" Nature Reviews, Neuroscience, vol. 4, May 2003, pp. 417-422.

* cited by examiner

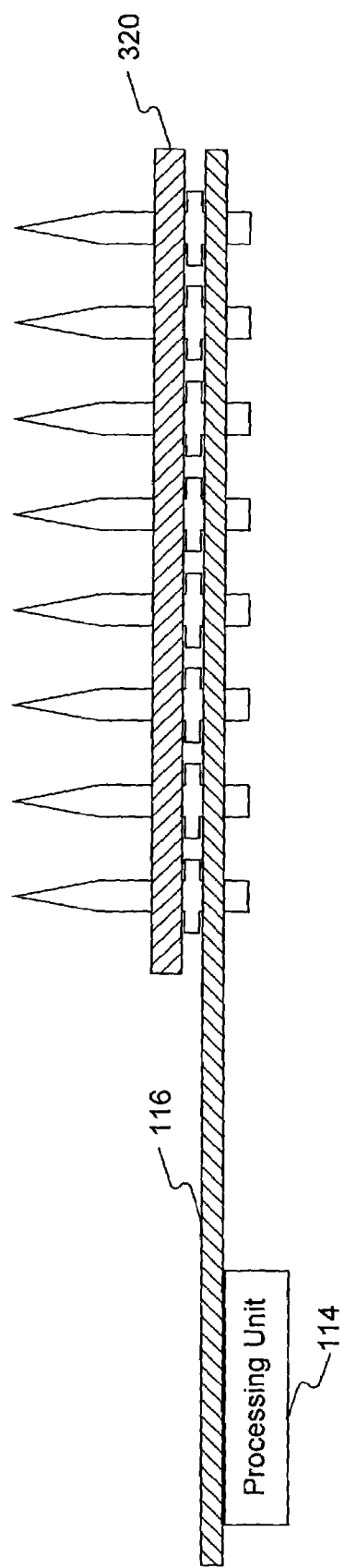

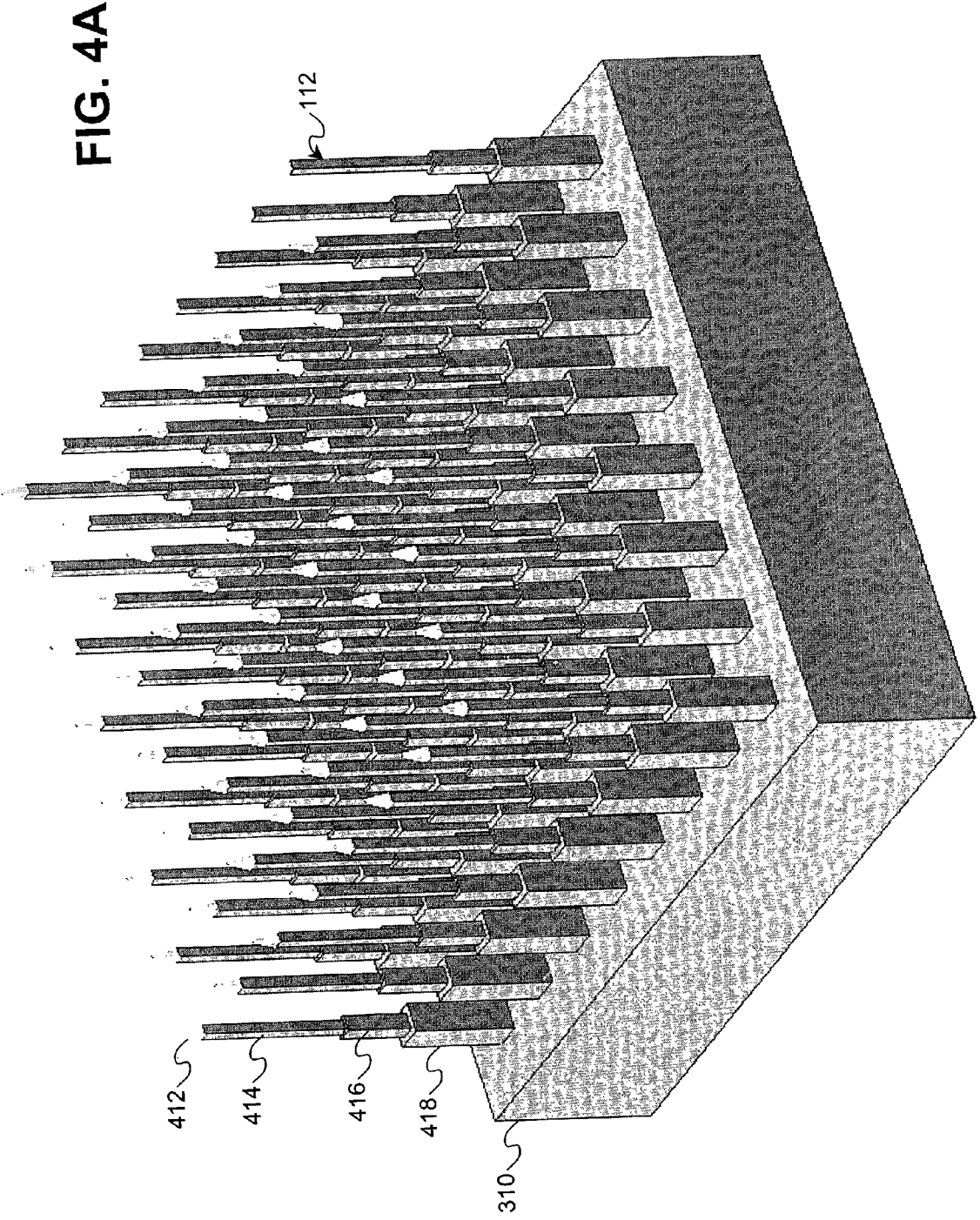

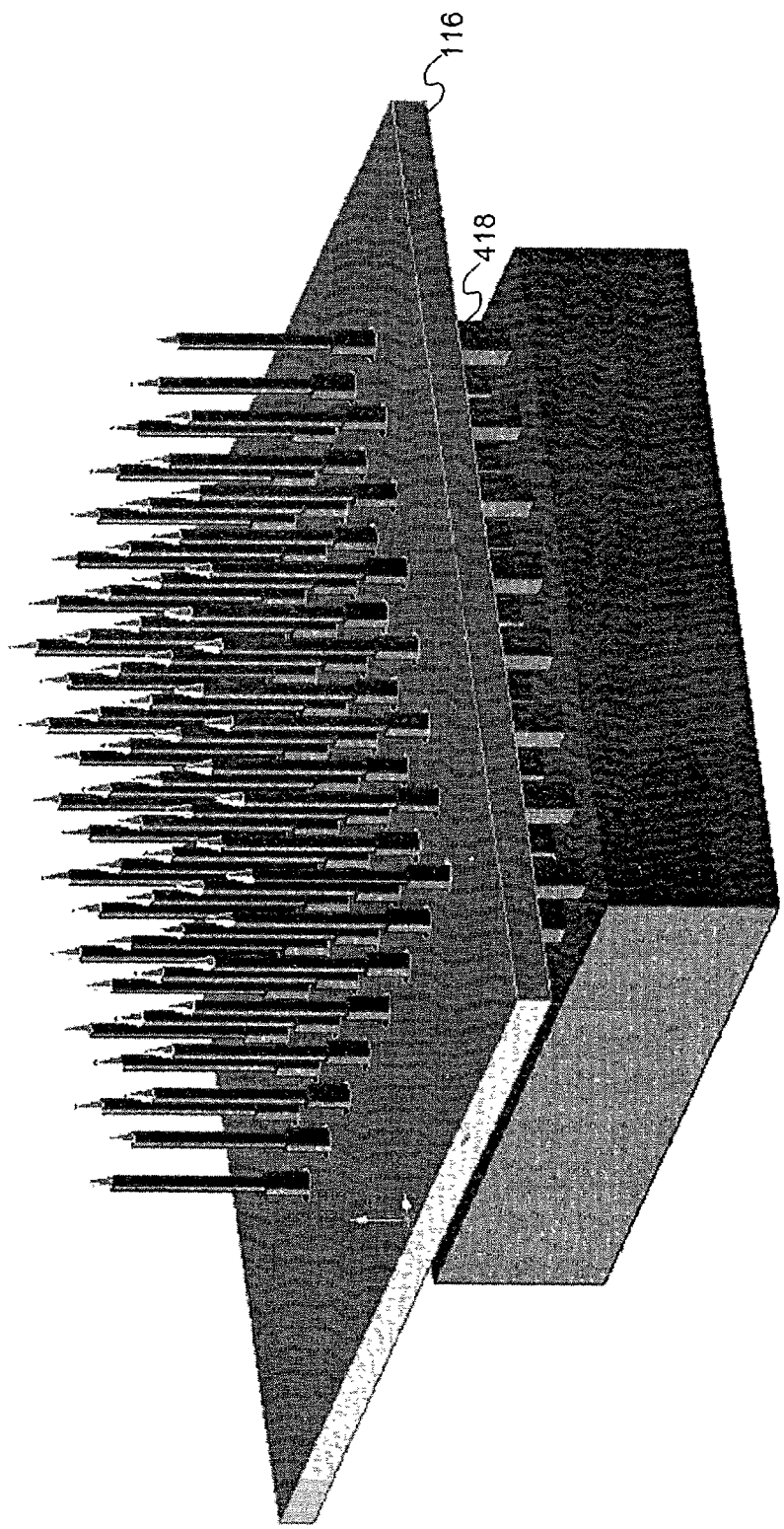

MICROSTRUCTURED ARRAYS FOR CORTEX INTERACTION AND RELATED METHODS OF MANUFACTURE AND USE

GOVERNMENT SUPPORT

The U.S. Government has certain rights in this invention as provided for by the terms of grant No. NS25074 and contract No. NO1-NS-9-2322 from N.I.N.D.S.

BACKGROUND OF THE INVENTION

Recent advances in neurophysiology have allowed researchers to study the activity of groups of neurons with high temporal resolution and in specific locations in the brain. These advances create the possibility for brain-machine interfaces allowing an amputee to control a prosthetic limb in much the same way that person would control a natural limb. Although noninvasive sensors, such as multi-channel electroencephalogram (EEG), have shown some promise as simple interfaces to computers, they do not currently offer the spatial resolution needed for prosthetic control. Current research into the electrical activity of small groups of neurons has thus been done primarily with arrays of microelectrodes inserted into the brain.

Current intra-cortical microelectrode recording systems can record electrical signals from groups of neurons. These systems typically use a microscopic tapered conductive element, insulated except at its tip, to record the neuron signals. Other conductor designs, such as blunt cut wires, may record single neurons, but have sub-optimal recording characteristics. Further, nearly all recording systems rely on arrays of fixed electrodes connected to data acquisition systems through long wiring or cable harnesses. The percutaneous connectors associated with these cables present a potential source of infection that limits the useful life of these systems. The cables themselves also present additional problems in the design of a prosthesis that must continue to function over many years and not interfere with the patient's daily life. For instance, the cables limit the patient's mobility by being tethered to a signal processing device. Relatively long cables may also present a source of electrical interference and may break after repetitive use.

The current microelectrode systems for recording single neurons can be grouped into two broad classes: those having microdrive mechanisms and those having fixed electrode arrays. Systems with microdrive mechanisms allow one to vertically position the electrodes in the brain tissue. Thus, a user can actively search for neurons of interest and accurately position the electrode tip near the soma of the neuron to improve the signal-to-noise ratio. These systems, however, have their disadvantages. First, even individual microdrive systems are bulky and cannot be fully implanted in a human. Second, microdrive systems typically cannot use more than a few dozen electrodes due to space limitations and the time it takes to independently position each electrode near a neuron.

Fixed electrode array systems overcome some of these problems, but have their own problems as well. Once placed in the brain, fixed electrode arrays can not be repositioned, so they rely on chance proximity to neurons. The most basic fixed electrode arrays record neural activity using multiple micro-wires or hatpin-like electrodes individually inserted into the brain. Because it can take a relatively significant amount of time to insert each electrode, however, these systems have not been widely used. More recently, wire bundles have been developed which are inserted into the cortex as a unit, but they lack features of ideal recording electrodes, such as tip shape, overall size, and impedance. In particular, the common square tip of such microwires can damage the cortex and can have difficulty penetrating the tough cerebral membranes, as well as brain tissue.

A major disadvantage of these fixed array systems is that they do not offer the ability to actively hunt for neurons since the electrode tips cannot be easily placed near the soma of the neurons. To help overcome this, large numbers of electrodes are inserted to increase the chance that the electrodes are positioned in close proximity to neurons. The input impedances of the electrodes may also be lowered to enhance their ability to record distant signals. Lowering the input impedance, however, also lowers the signal-to-noise ratio.

Accordingly, there is a need for a fixed microelectrode array system that may have numerous electrodes providing a high signal-to-noise ratio. Further, there is a need for a fixed array system that has a flexible design and that does not rely upon percutaneous cabling systems to communicate with a data acquisition system.

SUMMARY OF THE INVENTION

According to a first aspect of the invention, a method of manufacturing an electrode array system is disclosed. The method includes machining a work piece of an electrically conductive substance to create a plurality of electrodes extending from a base member. Each electrode has a corresponding base section. A nonconductive layer is provided around at least a portion of the base sections of the plurality of electrodes. The base member is removed from the plurality of electrodes, such that the plurality of electrodes are supported by the nonconductive layer.

Another aspect of the invention discloses an electrode array. The array includes a flexible nonconductive support layer and an array of electrodes. Each electrode has a base section and a tip section, where the base section of each electrode is inserted into the nonconductive layer, such that the electrodes are held together by the nonconductive layer. An electrical connection located on the base section of each electrode communicates with the respective electrode.

In yet another aspect of the invention, a brain implant system comprises an electrode configured to be inserted in a brain and for sensing electrical signals generated by brain neurons. A flexible wiring circuit is connected to the electrode and adapted to receive the neuron electrical signals sensed by the electrode. A processing unit receives the neuron electrical signals from the flexible wiring circuit. The processing unit further includes a detection module for detecting the occurrence of a neuron spike in the received neuron electrical signals. The processing unit also includes a transmitter for transmitting data reflecting the occurrence of each detected neuron spike.

In still another aspect of the invention, a method for operating a brain implant system, comprises: providing an electrode configured to be inserted in a brain and for sensing electrical signals generated by brain neurons; receiving the neuron electrical signals sensed by the electrode over a flexible wiring; receiving the neuron electrical signals from the flexible wiring and detecting the occurrence of a neuron spike in the received neuron electrical signals; and transmitting data reflecting the occurrence of each detected neuron spike.

Both the foregoing general description and the following detailed description are exemplary and are intended to provide further explanation of the embodiments of the invention as claimed.

BRIEF DESCRIPTION OF THE DRAWINGS

The accompanying drawings, which are incorporated in and constitute a part of this specification, illustrate various embodiments of the present invention, and, together with the description, serve to explain the principles of the invention. In the drawings:

FIGS. 3A to 3D illustrate exemplary process for making an electrode array consistent with an embodiment of the present invention;

FIGS. 4A to 4G illustrate an alternative, exemplary process for making an electrode array consistent with an embodiment of the present invention;

DESCRIPTION OF THE EMBODIMENTS

Reference will now be made in detail to the present embodiments of the invention, examples of which are illustrated in the accompanying drawings. Wherever possible, the same reference numbers will be used throughout the drawings to refer to the same or like parts.

Figure 1:
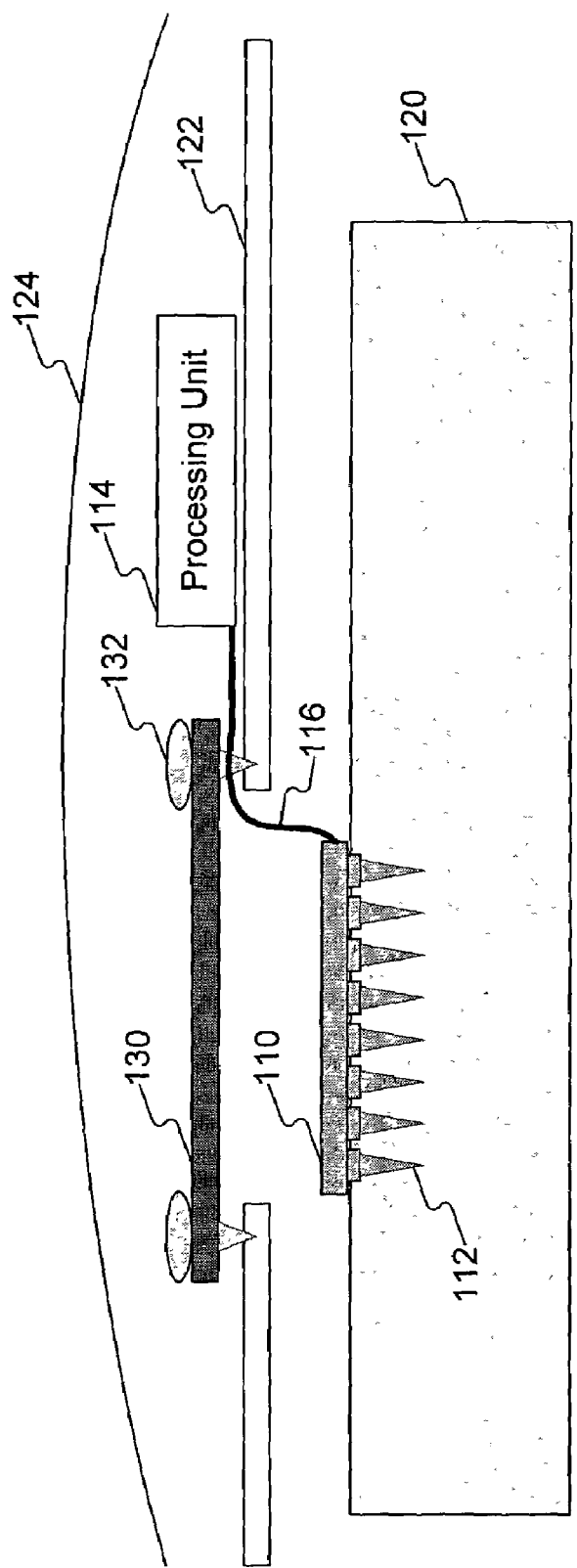
FIG. 1 is a diagram illustrating an exemplary brain implant system consistent with an embodiment of the present invention.

FIG. 1 generally illustrates a brain implant system consistent with an embodiment of the present invention. As shown in FIG. 1, the system includes an electrode array 110 inserted into a patient's cerebral cortex 120 through an opening in the skull 122. Array 110 may include a plurality of electrodes 112 for detecting electrical brain signals or impulses. While FIG. 1 shows array 110 inserted into cerebral cortex 120, array 110 may be placed in any location of a patient's brain allowing for array 110 to detect electrical brain signals or impulses.

Each electrode 112 may be connected to a processing unit 114 via wiring 116. Processing unit 114 may be secured to skull 122 by, for example, the use of an adhesive or screws, and may even be placed inside the skull if desired. A protective plate 130 may then be secured to skull 122 underneath the surface of the patient's skin 124. In one embodiment, plate 130 may be made of titanium and screwed to skull 120 using screws 132. However, the invention may use any of a number of known protective plates, such as a biological material, and methods for attaching the same to a patient's skull. Further, processing unit 114 and other surgically implanted components may be placed within a hermetically sealed housing to protect the components from biological materials.

Electrode array 110 serves as the sensor for the brain implant system. While the various figures in this specification illustrate electrode array 110 as having sixty-four electrodes 112 arranged in an 8×8 matrix, array 110 may include one or more electrodes having a variety of sizes, lengths, shapes, forms, and arrangements. Each electrode 112 extends into brain 120 to detect the electrical neural signals generated from the neurons located in proximity to the electrode's placement within the brain. Neurons may generate such signals when, for example, the brain instructs a particular limb to move in a particular way. Electrode array 110 is described in more detail with respect to FIGS. 3A to 3D and FIGS. 4A to 4G.

Electrodes 112 transfer the detected neural signals to processing unit 114 over wiring 116. As shown in FIG. 1, wiring 116 may pass out of the opening in skull 122 beneath protective plate 130. Wiring 116 may then run underneath the patient's skin 124 to connect to processing unit 114. Persons skilled in the art, however, will appreciate that arrangements other than the one shown in FIG. 1 may be used to connect array 110 to processing unit 114 via wiring 116. Wiring 116 is described in more detail below with respect to FIGS. 5A and 5B.

Processing unit 114 may preprocess the received neural signals (e.g., impedance matching, noise filtering, or amplifying), digitize them, and further process the neural signals to extract neural information that it may then transmit to an external computing device (not shown). For example, the external device may decode the received neural information into motor control signals for controlling a motorized prosthetic device or analyze the neural information for a variety of other purposes. Processing unit 114 is described in further detail with respect to FIG. 2A.

Figure 2A:
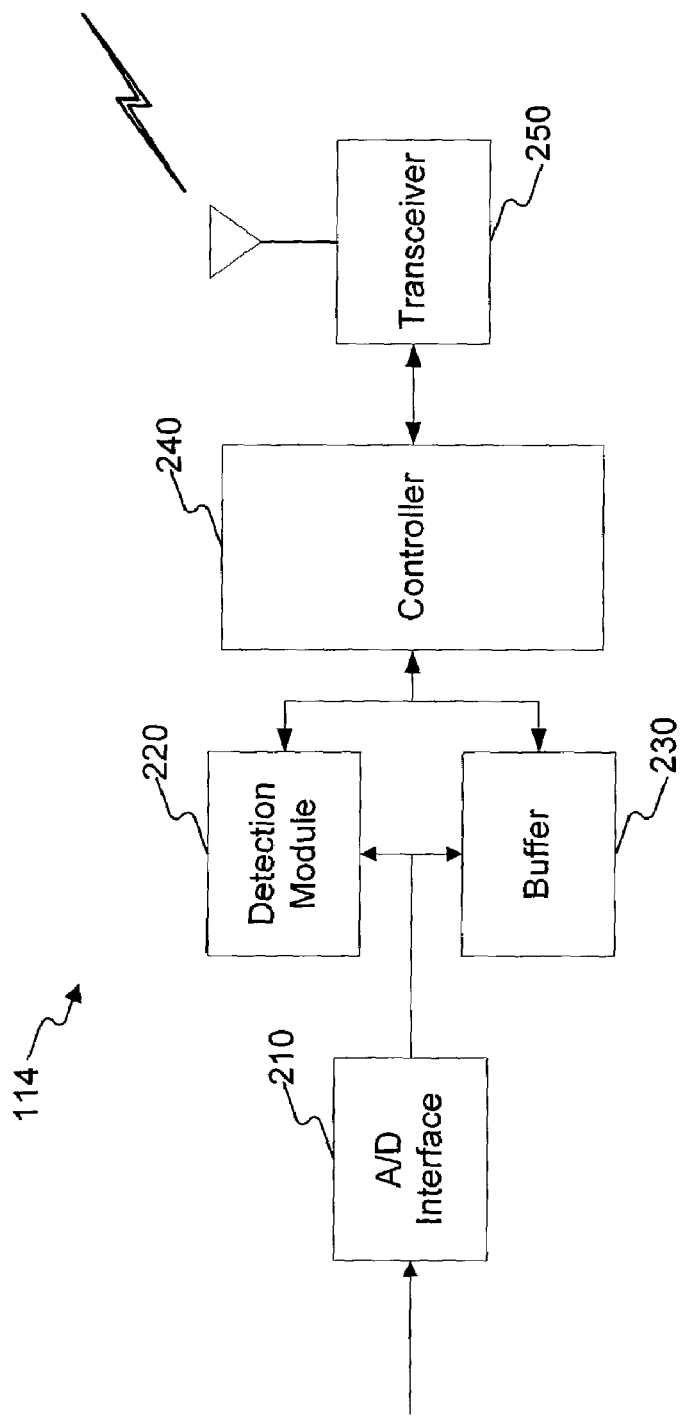
FIG. 2A is a block diagram of a neuron signal processing system consistent with an embodiment of the present invention.

FIG. 2A is a block diagram of a processing unit 114 consistent with an embodiment of the present invention. As shown in FIG. 2A, processing unit 114 may further include an analog-to-digital (A/D) interface 210, a detection module 220, a buffer 230, a controller 240, and a transceiver 250. In an exemplary embodiment, interface 210, module 220, and buffer 230 each may be implemented by a common field programmable gate array (FPGA), although other embodiments are possible. For instance, alternative embodiments may include dedicated hardware or software components for implementing subcomponents 210, 220, or 230, such as by using a microprocessor.

A/D interface 210 may include a plurality of A/D converters, each of which may receive the analog output from a corresponding electrode 112 or group of electrodes 112. Each A/D converter may amplify, digitize, and multiplex the signals received from the corresponding electrode(s) 112. In one exemplary embodiment, an amplification stage of A/D interface 210 may be implemented using a CMOS-based two-stage operational amplifier known to those skilled in the art, and selected to have a bandwidth of approximately 300–10 kHz and a gain of about 5000. However, processing units consistent with the present invention may also process other electrical neural signals, such as those in the 0–100 Hz range, for example.

For the exemplary embodiment of array 110 comprising an 8×8 matrix of electrodes, A/D interface 210 may include eight 12-bit, 37.5 kHz A/D converters, each of which receives the analog outputs from eight corresponding electrodes. In such a case, each A/D converter may multiplex the electrode channel signals received from a corresponding row or column of array 110. A/D interface 210 may, however, multiplex other groupings of the electrode channels using any number of A/D converters. For instance, A/D interface 210 may include one A/D converter that receives the analog outputs from all of the electrode channels to multiplex those signals into one signal. Alternatively, A/D interface 210 may simply convert the electrode channels into digital signals without multiplexing. In either case, interface 210 may then provide the digital signals to detection module 220.

Detection module 220 detects when a neuron has fired. The signal from a single neuron essentially comprises a series of electrical spikes. The brain encodes information according to the frequency or firing rate of these spikes, which is typically between 0 to 300 Hz. The spike itself may last about 1.5 ms and may have a peak-to-peak voltage of about 100 μV. In systems consistent with an embodiment of this invention, detection module 220 may detect the time a spike occurs since the neural information content is encoded in the timing between the spikes. Alternatively, module may detect the spike count over a predetermined time period or may detect instantaneous neural frequencies. In either event, by removing the inter-spike data and reducing the waveform to a time spike representation, module 220 may optimize the wireless communication bandwidth and minimize the storage requirements of the brain implant system. Buffer 230 may, however, also record information sufficient to determine the shape of the spike. The ability to determine the spike's shape may be needed in certain applications, such as when sorting which spikes come from which neurons.

To detect a spike, detection module 220 may detect whether the channel signal from A/D interface 210 meets a triggering event. Spike detection may be based on time, amplitude, or other aspects of the shape of the waveform. For example, module 220 may detect when the rising edge of a neural signal detected with a particular electrode 112 exceeds a predetermined threshold value in amplitude or time, or a combination of the two. Since the spike amplitude may vary among neurons, module 220 may vary the threshold value for each electrode 112 based on the particular neuron(s) being detected by that electrode. In an exemplary embodiment, detection module 220 may include a programmable 12-bit threshold for setting the threshold level(s).

Buffer 230 may be implemented by using a pre-trigger and a post-trigger buffer memory. For instance, a small ring buffer may temporarily pre-store the digital data of a channel prior to a triggering event detected by detection module 220. The pre-trigger buffer memory may thus store those samples corresponding to the spike's shape or other features (e.g., spike slope), prior to the triggering event. Buffer 230 may also include a separate pre-trigger buffer for each channel or electrode 112, which may store the samples from each channel, according to an exemplary embodiment. Channel data obtained after the triggering event may then be stored directly in the post-trigger buffer memory to record the time each spike occurs and/or the spike shape. In one exemplary embodiment, buffer 230 stores 1.65 ms of recorded data per spike. Alternatively and/or additionally, if no spike is detected, the contents of buffer 230 may be cleared and/or overwritten.

Upon triggering, buffer 230 may then output the data of both the pre-trigger and post-trigger buffer memories to transceiver 250. If buffer 230 outputs neural information faster than transceiver 250 may transmit that information, then buffer 230 may temporarily store the outputted data in a transmit buffer (not shown). Further, transceiver 250 may also transmit only the time of the triggered event of each detected neuron signal to increase the transmission rate.

Controller 240 may act as an interface between transceiver 250 and A/D interface 210, detection module 220, and buffer 230. Controller 240 may also perform certain other control functions, such as setting the trigger threshold level of module 220 or setting the size of pre-trigger or post-trigger buffers of buffer 230. In addition, controller 240 may be used to select particular electrode channels for processing and outputting by transmitter 250. Controller 240 may also manage the power resources of the electrode array system 100. To each of these ends, controller 240 may include an I/O interface allowing a user to program controller 240 to perform the above or other control functions. A user may thus program controller 240 by transmitting control signals from an external control device (not shown) to transceiver 250, which may then forward the control information to controller 240.

Transceiver 250 provides a wireless communication link between processing unit 114 and an external device (not shown). In particular, transceiver 250 receives the pre-trigger and post-trigger data stored in buffer 230 for transmission to the external device for further processing and storage. Transceiver 250 may transmit the data using "Bluetooth" technology or according to any other type of wireless communication standard, including, for example, code division multiple access (CDMA), wireless application protocol (WAP), or infrared telemetry. Transceiver 250 may also receive control information using either of the above communication techniques.

Figure 2B:
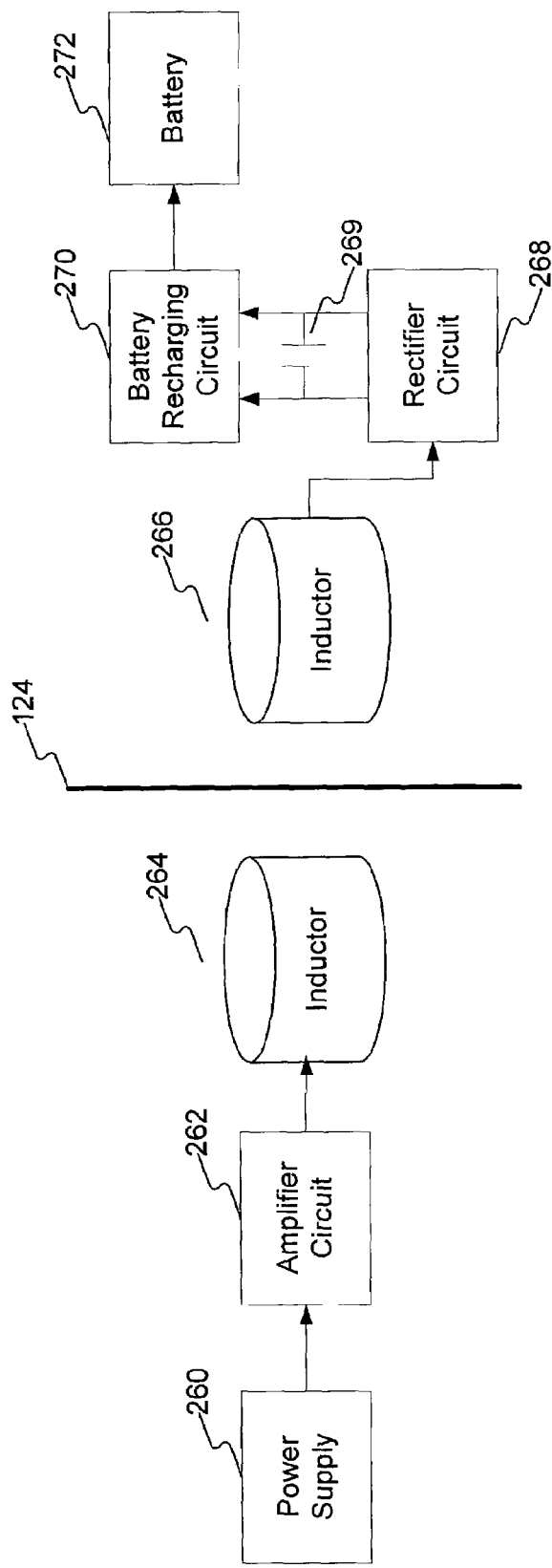
FIG. 2B is a block diagram of a power supply system consistent with an embodiment of the present invention.

Processing unit 114 may also include a power supply (not shown in FIG. 2A) for the brain implant system. FIG. 2B is a block diagram of an exemplary power supply system consistent with an embodiment of the present invention. While the power supply system of FIG. 2B allows the implanted power supply to be recharged, other power supply systems may be used (such as a typical battery source) that need to be replaced when their power is exhausted. As shown in FIG. 2B, a power supply system consistent with the invention may include a power supply 260, an amplifier 262, an outside coil or inductor 264, an inside coil or inductor 266, a rectifier circuit 268, a battery recharging circuit 270, and a battery 272. Components 260, 262, and 264 are located outside of the patient's body (i.e., outside skin 124) and components 266, 268, 270, and 272 are located inside the patient's body.

While each of the components of the power supply system of FIG. 2B are individually known to those skilled in the art, the particular hardware chosen to implement components 266, 268, 270, and 272 may be advantageously chosen based on size, heat requirements, and biocompatibility. For instance, a preferred embodiment would implement components 266, 268, 270, and 272 by using hardware having a small size, low heat dissipation, and a high biocompatibility with the natural tissue inside the patient.

Power supply 260 may be any AC power supply, such as a standard 120 volt AC power source. Amplifier 262 receives an AC voltage signal from supply 260, amplifies it, and applies the amplified AC voltage signal to inductor 264. When inductor 264 is activated and placed in close proximity to inductor 266, inductor 264 will induce a current in inductor 266. The induced current then creates an AC voltage on the output terminals of inductor 266, which is then applied to rectifier circuit 268. Rectifier 268 then converts the induced AC voltage signal to a DC voltage signal in a manner known to those skilled in the art. FIG. 2B further shows an optional capacitor 269 for filtering the rectified voltage signal. In particular, capacitor 269 may further limit any AC voltage signal levels that may still be present on the rectified output signal and thereby present a cleaner DC voltage signal. Battery recharging circuit 270 then receives the DC voltage signal for charging battery 272 located inside the patient. In an exemplary embodiment, battery 272 is a lithium-polymer 3.6 V battery.

Figure 3A:
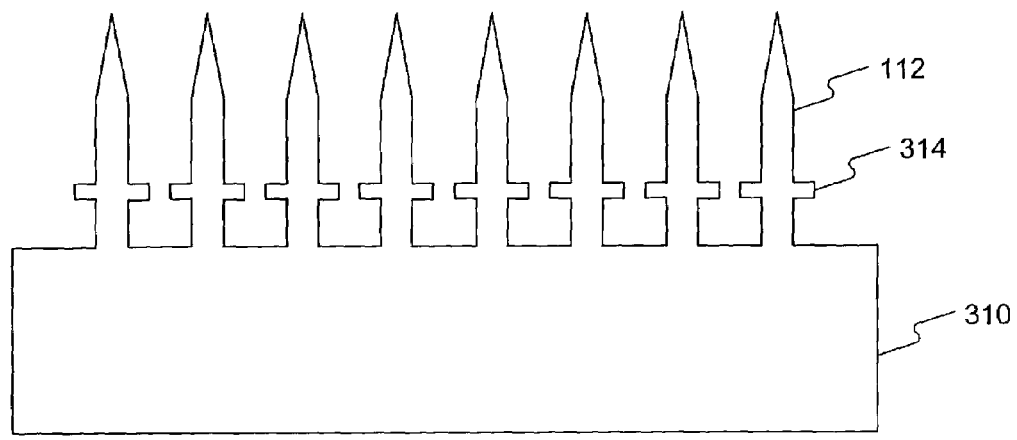
Figures 1, 3A:
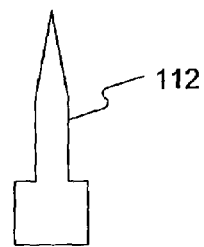

FIGS. 3A to 3G illustrate exemplary manufacturing processing steps for preparing an electrode array consistent with an embodiment of the present invention. In particular, FIG. 3A shows a work piece or block of electrically conductive material 310 including a plurality of electrodes 112. While an exemplary embodiment includes using titanium as material 310, a number of other conductive materials may be used, including, for example, stainless steel, steel, titanium nitride, a titanium-aluminum-vanadium alloy, tungsten carbide, copper, or doped silicon. Electrodes 112 may be formed from material 310 by applying a wire electrical discharge machining (wire EDM) technique known to those skilled in the art. In particular, wire EDM may be used to precisely machine a raw block of electrically conductive material 310 to form electrodes 112. Array 110 may be formed by performing a wire EDM cut through one plane, rotating array 110 ninety degrees, and then performing a second wire EDM cut through a second plane. Other known manufacturing methods may, however, be used to micromachine conductive material 310, such as by using a laser or a diamond saw.

Further, a chemical etching process may also be applied to further machine electrodes 112. For instance, the machined array of FIG. 3A may be placed in an etching bath to further etch the electrode surfaces. When material 310 is titanium, for example, a heated hydrochloric or hydrofluoric acid bath may be used to etch the electrode surfaces. By an etching process, electrodes 112 of finer widths may be obtained. This process also removes the oxide layer from the electrode surfaces and smoothes those surfaces, a desirable step before forming additional coatings on array 110.

Figures 2, 3A:
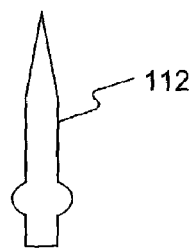

FIG. 3A shows electrodes 112 as having a tapered shape at their tips. In an exemplary embodiment, each electrode 112 may have a width of about 80 μm and taper to a point over the top 50 μm of its length. Further, FIG. 3A also shows that a base section of electrodes 112 may have a platform portion 314. Portions 314 may serve as a platform for securing a support layer, which is described below with respect to FIGS. 3B and 3C. Rather than having platforms 314, however, electrodes 112 may include a stepped lower base portion (e.g., as shown in FIG. 3A-1) or a rounded lower base portion (e.g., as shown in FIG. 3A-2), which may alternatively serve as a platform for supporting the support layer. Moreover, electrodes 112 may have a variety of shapes, such as a continuous width shape (i.e., with no platform or stepped base section), a conical shape, a stepped-pyramidal shape, or a tapered shape different than that shown in FIG. 3A. Electrodes 112 may also have a variety of cross-sectional shapes, such as a rounded cross-section (which may be formed by a chemical etching process) or a rectangular, square, or hexagonal cross-section (which may be formed by the wire EDM technique). Moreover, as used herein, an electrode's "base section" refers broadly to the end portion of electrode 112 opposite the electrode's tip, without referring to the electrode's shape or width.

Electrodes 112 of array 110 may also differ in length to sense particular neurons located at different depths in cortex 120. For instance, electrodes 112 may increase in length from one side of array 110 to the other. Electrodes 112 may also vary in both length and width from other electrodes in array 110, such that a given electrode 112 is either longer or shorter, or wider or narrower, than the electrode adjacent to it. For instance, array 110 may include shorter electrodes between 0.1 mm to 8 mm in length and/or longer electrodes between 0.3 mm to 50 mm in length. Further, for electrodes 112 to record signals from common neurons, the spacing between electrodes may be less than 50 μm, while the spacing may be more than 400 μwhen electrodes 112 record signals from different neurons.

Electrode arrays 110 consistent with the invention may also arrange electrodes 112 in a number of ways. For example, electrodes 112 may be arranged in a one-dimensional or two-dimensional matrix, according to a predefined pattern, or in a random order. One exemplary pattern in which electrodes 112 may be arranged is a honeycomb-like hexagonal pattern. As described above, however, any type of pattern or arrangement of electrodes 112 may be used to form array 110.

Depending upon the composition of conductive material 310, electrodes 112 may be coated with a separate conductive layer (not shown). The conductive layer may only be necessary if conductive material 310 is not biocompatible with the neural tissue and cerebro-spinal fluid or if the electrical characteristics require a coating (e.g., to avoid junction potentials at the electrode tips). An exemplary embodiment may include coating electrodes 112 with platinum by an electroplating process or other deposition method. The deposited layer may also improve the sensitivity of the electrode and may also prevent oxidation of the electrode. Electrode arrays 110 consistent with the present invention may also use other conductor materials besides platinum, such as gold or titanium nitride, formed by electroplating or other types of formation processes, such as vapor deposition or electron beam deposition. Further, the entire structure of FIG. 3A or just the tips of electrodes 112 may be coated with the conductive material.

An insulating layer (not shown) may also be applied to electrodes 112. Except for the electrode tip used to record the neural signals, the insulating layer may cover the whole electrode. The insulating layer may be removed from the electrode tips (e.g., by laser ablation, plasma etching, or chemical etching), or may be prevented from being formed on the tips (e.g., by a masking procedure). In this way, conduction is allowed only through the tips and single neurons can be better isolated from one another. In the exemplary embodiment, all but the top 50 μof each electrode 112 are insulated with Paralene by a vapor deposition process. Other insulating materials, such as glass, silicon nitride, polyimide, an epoxy, or other plastics or ceramics, may be used instead.

Figure 3B:
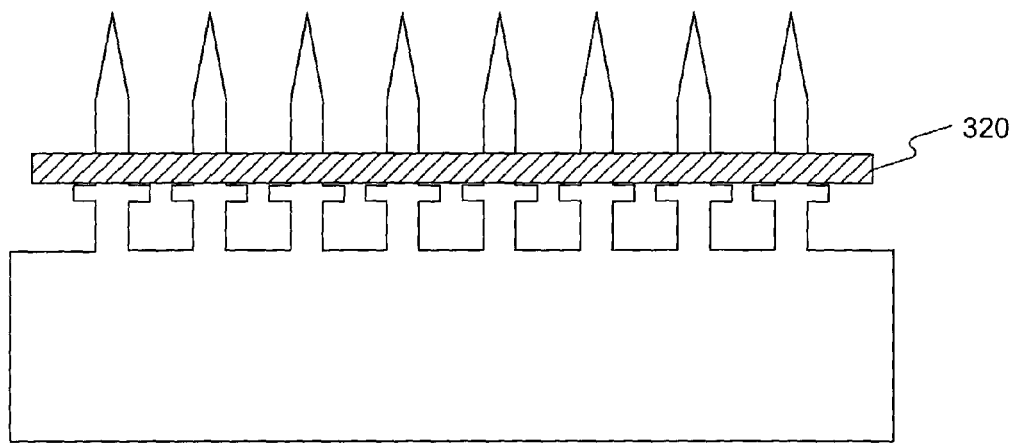

As shown in FIG. 3B, a support layer 320 may then be placed over electrodes 112 to electrically isolate electrodes 112 and to support electrodes 112 during the cutting process described below with respect to FIG. 3O. Layer 320 may have a number of corresponding openings for receipt of electrodes 112. Support layer 320 may slide down over electrodes 112 until, for example, it reaches the bottom platform sections 314 of each electrode 112. Each hole or opening in layer 320 may have a diameter sized to securely receive each electrode 112, while compensating for any positional tolerances from a drilling or laser process when forming the holes. In the exemplary embodiment, support layer 320 is a flexible material, such as polyimide, parylene, or silicone. Layer 320 may also be formed using materials having a flexibility that changes over time or under some other condition (e.g., having a flexibility that changes in response to the brain's heat).

Figure 3C:
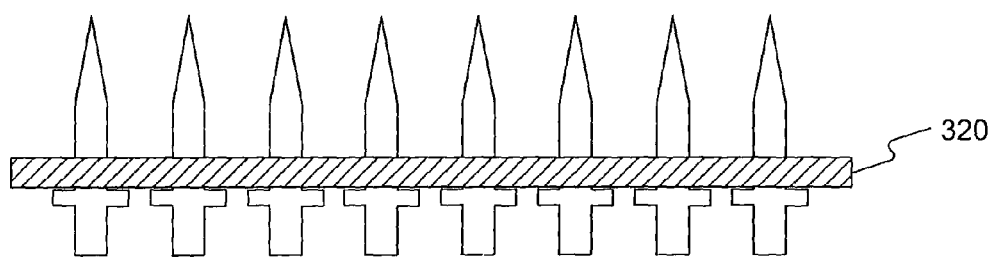

An optional step may include applying an epoxy coating (not shown) to electrodes 112 and support layer 320. The epoxy coating may, however, be applied after electrodes 112 are cut as described below with respect to FIG. 3C. After support layer 320 has been placed over electrodes 112, the bases of electrodes 112 may be cut using a wire EDM technique to separate electrodes 112 from block 310. FIG. 3C illustrates array 110 after electrodes 112 have been cut or separated from block 310.

After cutting electrodes 112, wiring 116 may then be placed over the cut ends of electrodes 112, as shown in FIG. 3D, to connect electrodes to processing unit 114. Like support layer 320, wiring 116 may have a number of corresponding openings for receipt of electrodes 112. While FIG. 3D shows these openings as passing entirely through wiring 116, the openings may alternatively be formed as depressions in wiring 116, such that electrodes 112 may fit within the opening or depression, but not pass entirely through wiring 116. In either case, each hole or opening may have a diameter sized to securely receive each electrode 112, while compensating for any positional tolerances from a drilling or laser process when forming the holes. Wiring 116 may then slide over electrodes 112 until, for example, it reaches the platform sections 314 of each electrode 112. Wiring 116 may then be electrically connected to electrodes 112. Further, the cut array assembly may be placed in a holder (not shown) to hold electrodes 112 in place when aligning and lowering wiring 116 over electrodes 112. In the exemplary embodiment, wiring 116 may also be formed of a flexible material, such as polyimide, parylene, or silicone. Wiring 116 is described in more detail below with respect to FIGS. 5A and 5B.

Figure 4B:
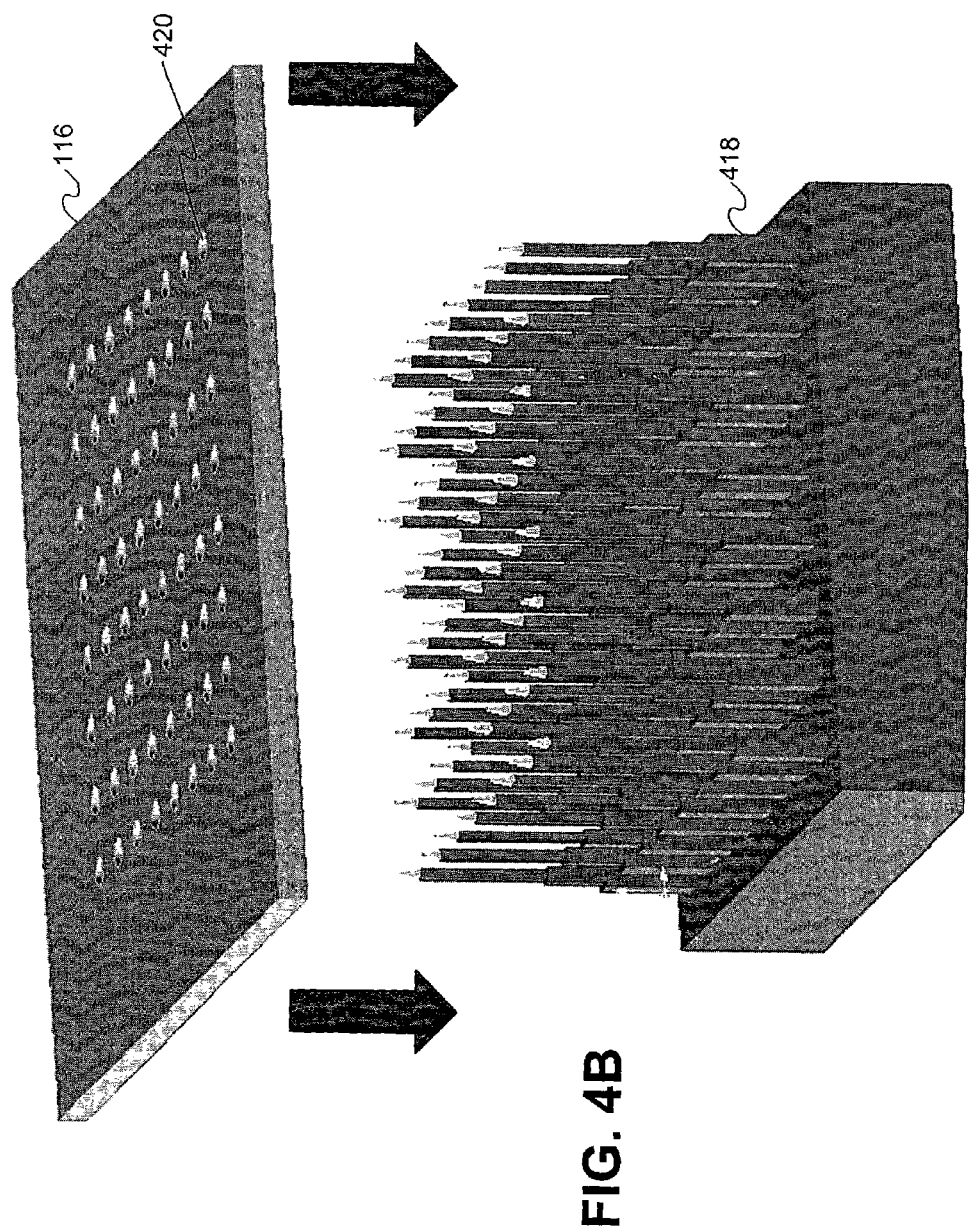

FIGS. 4A to 4G illustrate alternative, exemplary manufacturing processing steps, consistent with an embodiment of the present invention, for making an electrode array. In particular, FIG. 4A shows a block of electrically conductive material 310 including a plurality of electrodes 112. The electrodes of FIG. 4A may be formed using the processes described above with respect to FIG. 3A. As shown in FIG. 4A, however, electrodes 112 have a stepped-pyramidal shape similar to that shown in FIG. 3A-1, in which the electrodes 112 have stepped decreases in width from bottom to top. In an exemplary embodiment, each electrode 112 may have a tapered tip portion 412 and stepped base sections 414, 416, and 418 of increasing widths. As described above, however, electrodes 112 may have a variety of shapes, including continuous width shapes and stepped-pyramidal shapes having more or less than the three different width sections shown in FIG. 4A. Moreover, as stated above, an electrode's "base section" refers broadly to the end portion of electrode 112 opposite the electrode's tip, without referring to the electrode's shape or width.

As shown in FIG. 4B, wiring 116 may then be placed over electrodes 112. As shown in FIG. 4B, and as described above with respect to FIG. 3D, wiring 116 may have a number of corresponding openings 420 for receipt of electrodes 112. Wiring 116 may slide down over electrodes 112 until, for example, it reaches the bottom base section 418 of each electrode 112. FIG. 4C illustrates wiring 116 in its lowered position.

Figure 4D:
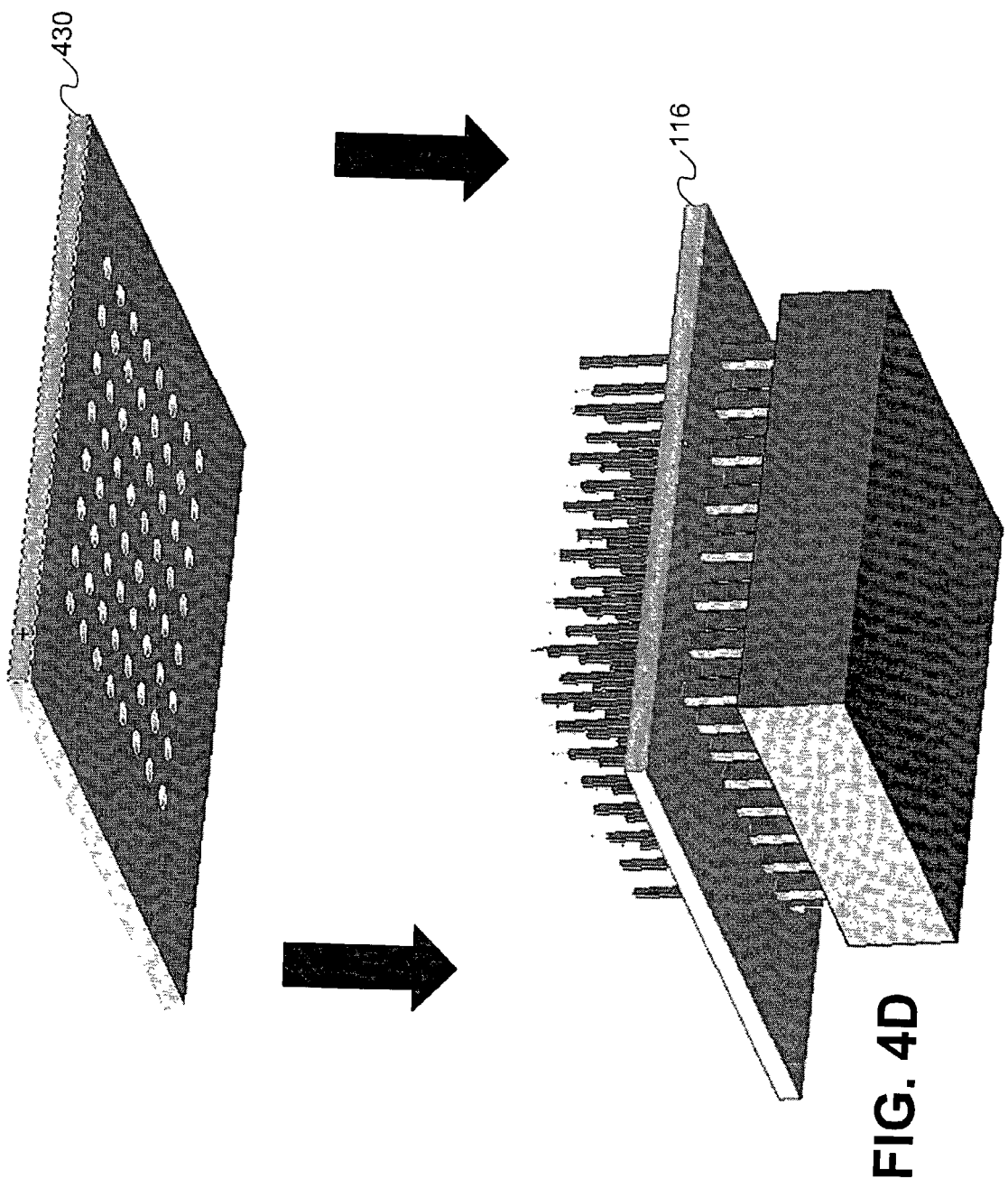
Figure 4E:
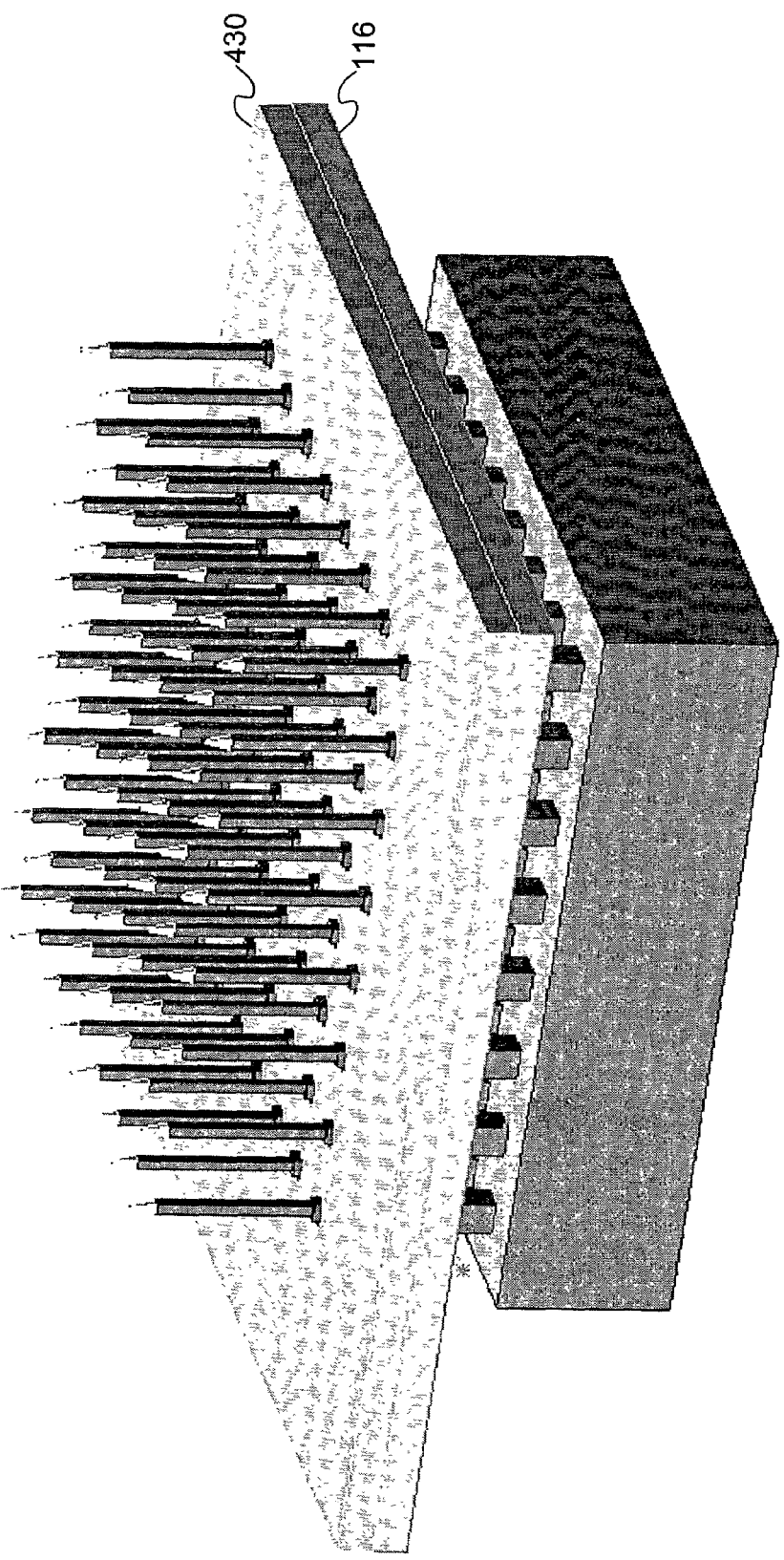
Figure 4F:
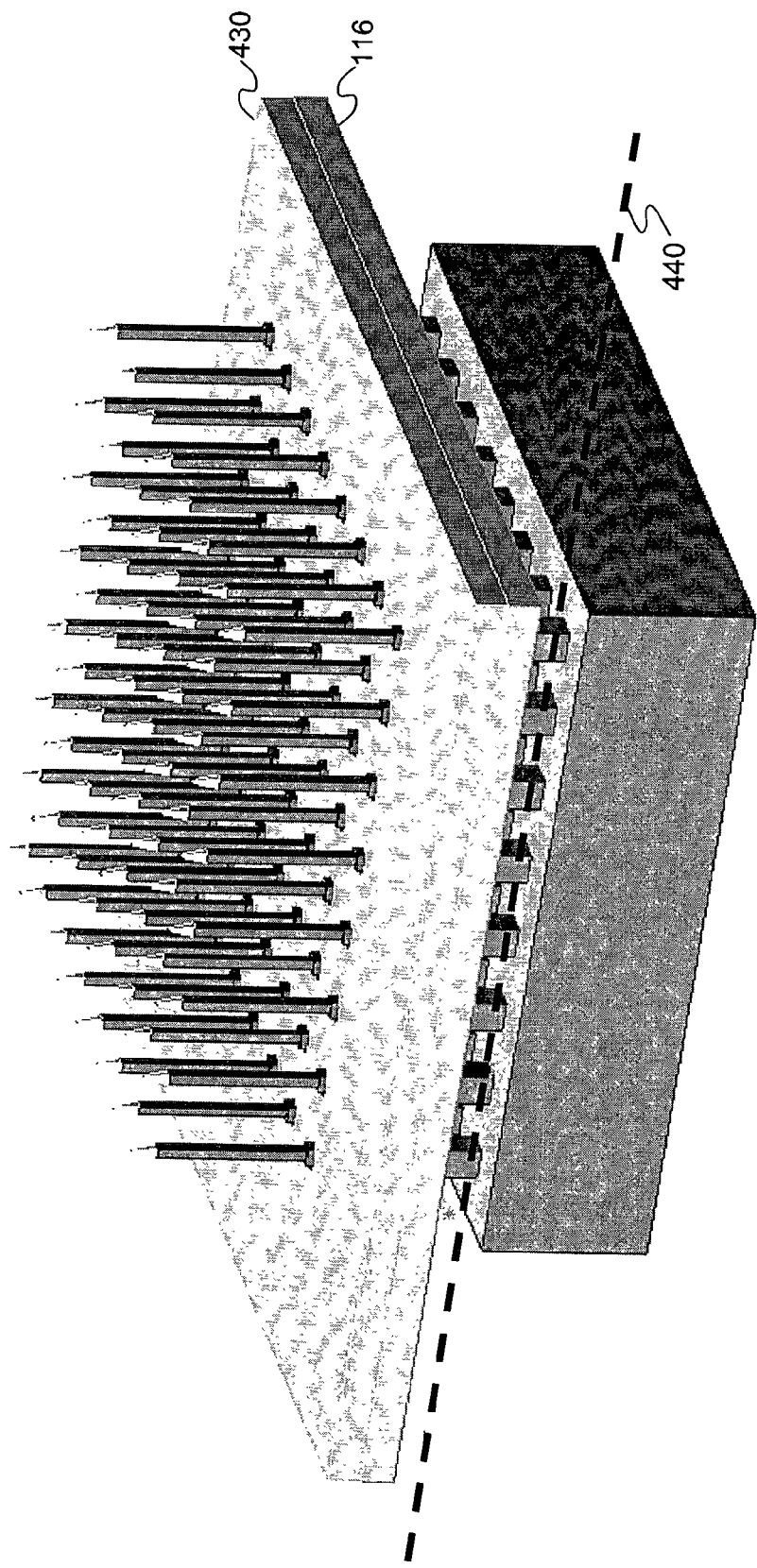
Figure 4G:
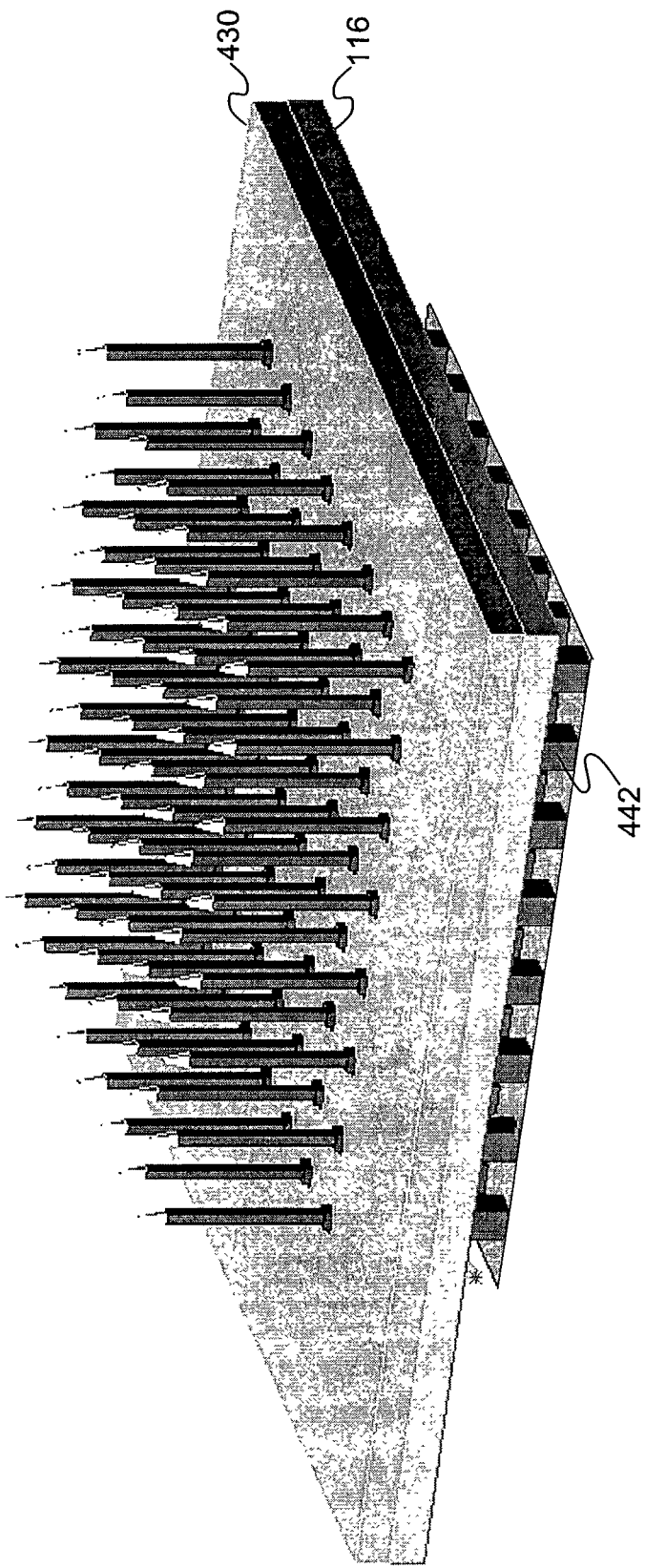

FIG. 4D shows an optional step of applying an epoxy coating 430 to electrodes 112 and wiring 116. Epoxy coating 430 may, however, be applied after electrodes 112 are cut as described below with respect to FIG. 4F. FIG. 4E shows the epoxy coating 430 lowered until it rests on top of wiring 116. While FIGS. 4D and 4E show epoxy coating 430 as having a sheet-like form, epoxy 430 may take a variety of forms, such as a more fluid-like form for coating array 110. After wiring 116 and epoxy coating 430 have been placed over electrodes 112, electrodes 112 may be cut along dashed line 440 shown in FIG. 4F by using a wire EDM technique. After cutting electrodes 112, their cut ends form square connector pads 442 which may then be soldered or otherwise electrically connected to the electrical contacts of wiring 116. FIG. 4G shows electrode array 110 after electrodes 112 have been cut.

By fabricating electrode array 110 according to the manufacturing methods discussed above with respect to FIGS. 3A–3D and FIGS. 4A–4G, array 110 may have an improved degree of flexibility over conventional fixed electrode arrays. This improved flexibility may be created by supporting the electrodes 112 removed from base 310 with either support layer 320 or flexible wiring 116. In particular, electrodes 112 are essentially supported and held together by their being inserted into the openings of support layer 320 or flexible wiring 116. Because layer 320 and wiring 116 can each be made flexible, array 110 can also then be flexible. This flexibility is an important feature of the present invention since it allows array 110 to better conform to the contours of the patient's brain and to be more compliant near blood vessels. However, systems and methods consistent with the invention may use electrode arrays 110 with limited flexibility.

Moreover, electrode arrays 110 consistent with the present invention may be manufactured by methods other than those discussed above with respect to FIGS. 3A–3D and FIGS. 4A–4G. For example, after fabricating electrodes 112, the base section of each individual electrode may be attached directly to a surface of wiring 116. According to this alternative manufacturing method, wiring 116 would not need any through-hole (e.g., opening 420) for receiving electrodes 112. The end of each electrode 112 may simply be placed on the surface of wiring 116 for attachment (e.g., by a bumping or soldering method).

Figure 5A:
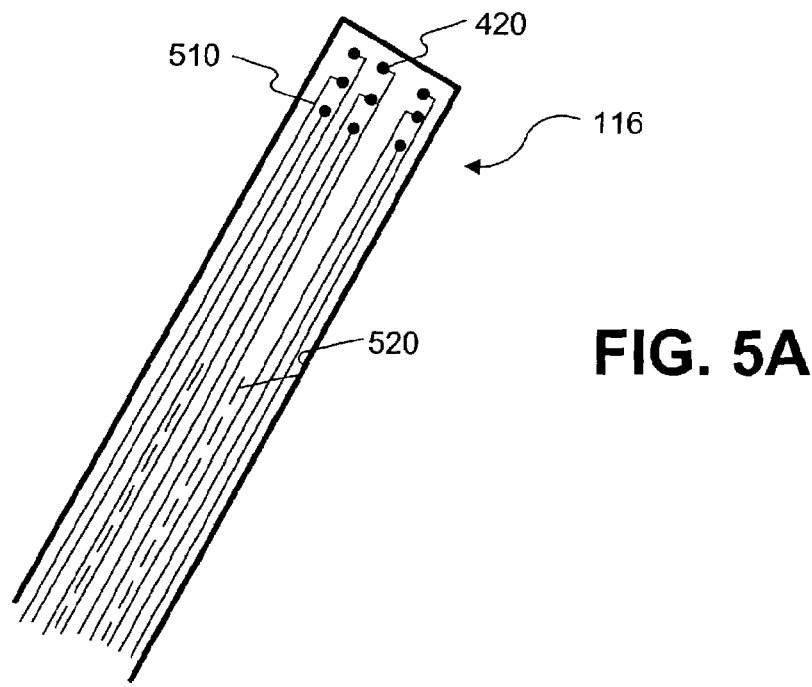
FIGS. 5A and 5B illustrate an exemplary wiring, consistent with an embodiment of the present invention, for attachment to an electrode array.
Figure 5B:
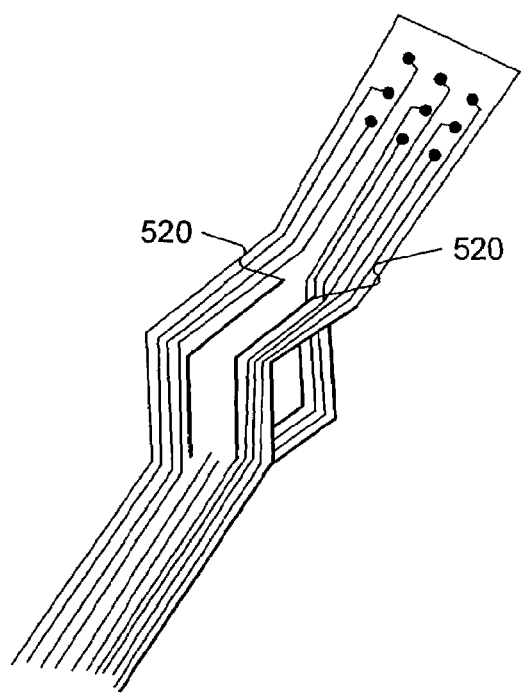

FIGS. 5A and 5B illustrate an exemplary embodiment of a wiring 116 consistent with the present invention. As shown in FIG. 5A, wiring 116 may include openings 420 for receiving electrodes 112 of array 110. A conductor 510 is connected to each opening 420 for transferring the neural signals received from an electrode 112 inserted into the corresponding opening. Conductors 510 may then connect to processing unit 114 using, for example, fine-pitch surface mount connectors.

As described above, wiring 116 may be a flexible circuit board or micro-ribbon cable made of polyimide, parylene, or silicone. In one exemplary embodiment, wiring 116 may comprise a single nonconductive layer of a polyimide-based flexible substrate having, for example, a thickness of up to approximately a 200 µm, and include conductors 510 having about a 25–50 µm diameter with a spacing of about 25–150 µm between adjacent conductors. This exemplary embodiment of wiring circuit 116 provides for a wiring connector having small dimensions and flexibility, while also having a good yield during manufacturing. Wiring circuits 116 consistent with the invention are not limited to these sizes, however, and those skilled in the art will appreciate that other sizes and types of wiring circuits may be used to connect electrode array 110 to processing unit 114.

A milling or laser machining process may then be used to create corresponding openings 420 for each conductor 510. In the exemplary embodiment, each opening 420 in wiring 116 may have a diameter sized to securely receive each electrode 112, while compensating for any positional tolerances from a drilling or laser process when forming the holes.

As shown in FIG. 5B, wiring 116 may also include slits 520 between conductors 510 at various points along the length of wiring 116. As shown in FIG. 5B, slits 520 may provide circuit 116 with three-dimensional flexibility to help reduce tethering forces described below. Slits 520 may be made by using a laser to make cuts on wiring 116 between the parallel conductors 510. Slits 520 may run up to the length of wiring 116. To prevent excessive bending of wiring 116 near its attachment to electrode array 110, a stiffener may also be added to wiring 116. For instance, a hardening resin or epoxy may be applied to the area where wiring 116 attaches to electrode array 110, as also discussed above with respect to FIG. 4D.

The flexibility between electrode array 110 and processing unit 114 created by wiring 116 offers several advantages. For instance, wiring 116 may reduce tethering forces created when the brain moves relative to the skull. If not reduced, these tethering forces may cause the position of electrode array 110 to move relative to the brain. To reduce these forces, an exemplary embodiment of wiring 116 has a horizontally flat shape where its width is much larger than its thickness. Wiring 116 thus has a lower stiffness for up-down brain shifts. Accordingly, by making slits 520 of sufficient lengths, wiring 116 may have minimum stiffness within the maximum expected range of motion. Wiring 116 may then allow electrode array 110 to move with the brain as it shifts relative to the skull. In this way, brain implant systems of the present invention may sustain relative brain shifts of up to 2 mm, which may result from cardiac and respiratory rhythms or other mechanical perturbations. Further, as an alternative to slits 520, wiring 116 may be coiled along its length or bent into an accordion-style staircase.

Figure 6A:
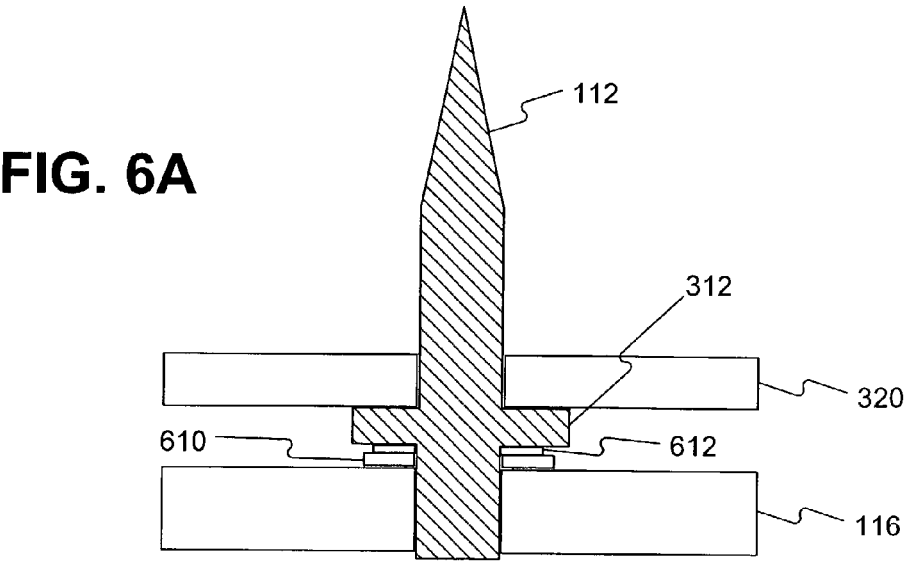
FIG. 6 illustrates an exemplary method, consistent with an embodiment of the present invention, for connecting an electrode to a wiring.
Figure 6B:
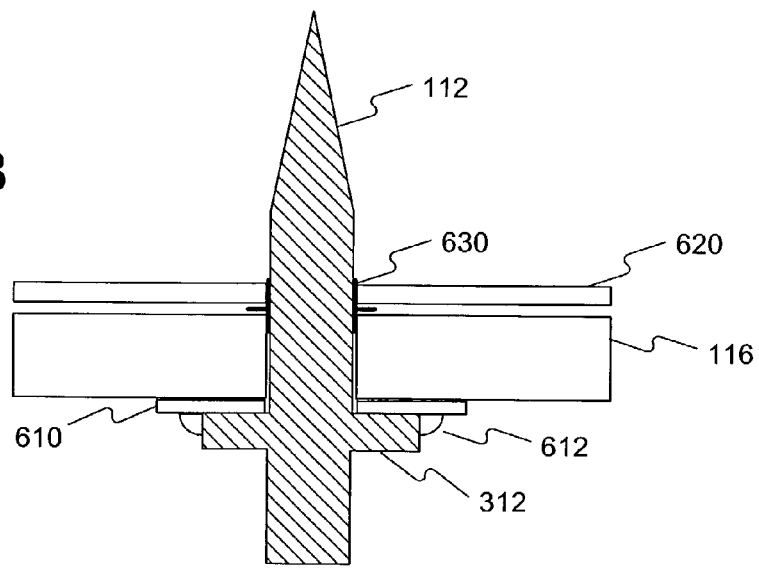

In an exemplary embodiment, a flip chip mounting method based on stud bumping or other bumping method may be used to connect wiring 116 to electrodes 112 of array 110. FIGS. 6A and 6B illustrate exemplary stud bumping mounting methods for the respective arrays manufactured according to the processing steps of FIGS. 3A to 3D and the processing steps of FIGS. 4A to 4G. Those skilled in the art will appreciate, however, that FIGS. 6A and 6B are intended to be exemplary of how known bumping techniques may be used to connect wiring 116 to array 110. Further, other attachment methods may also be used to mount wiring 112 to the array 110, such as by using a conductive epoxy.

FIG. 6A shows an electrode 112 inserted through an opening of support layer 320, as described above with respect to FIGS. 3B and 3C. To mount wiring 116, electrical contact pads 610 may be formed on wiring 116 near the openings 420 for receiving electrodes 112. Solder bumps 612 may then be disposed on pads 610. When wiring 116 is then placed against platform portions 312 of electrodes 112, solder bumps 612 are deformed and create an electrical connection between pads 610 and platform portions 312 of electrodes 112. While FIG. 6A shows contact pads 610 and solder bumps 612 placed on the side of wiring 116 facing support layer 320, pads 610 and bumps 612 may alternatively be placed on the other side of wiring 116 for connecting wiring 116 to electrodes 112.

In the exemplary embodiment of FIG. 6B, electrode 112 may be inserted through an opening 420 of wiring 116 until, for example, platform portion 312 of electrode 112 makes contact with electrical contact pads 610 formed on wiring 116 and mates with wiring 116. Solder 612, or other wire bonding methods or materials, may then be added to secure the electrical connection of electrode 112 to pads 610 and hence to wiring 116. A biocompatible polymer layer 620 may then be added on top of wiring 116 and an epoxy 630 may be applied to the space between electrode 112 and the opening 420 in wiring 116. Epoxy 630 may hold electrodes 112 in place for the cutting process described above with respect to FIGS. 4F and 4G. Further, this arrangement may cause any overflow of epoxy 630 from going between wiring 116 and the biocompatible polymer layer 620. By doing so, this will prevent epoxy 630 from leaking beyond the bottom of wiring circuit 116 and breaking the electrical contact between electrode 112 and the pads 610.

Accordingly, wireless brain implant systems and methods for using and manufacturing the same, have been described above. While this invention has been particularly shown and described with references to preferred embodiments thereof, it will be understood by those skilled in the art that various changes in form and details may be made therein without departing from the scope of the invention encompassed by the appended claims. For example, array 110 may be used to supply electrical impulse signals to cortex 120 in addition to sensing neural signals. Thus, array 110 may be used with neural stimulation techniques and tools known to those skilled in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A brain implant system comprising:
an electrode configured to be inserted in a brain and for sensing electrical signals generated by brain neurons;
a flexible wiring circuit connected to the electrode and adapted to receive the neuron electrical signals sensed by the electrode; and
a processing unit for receiving the neuron electrical signals from the flexible wiring circuit, wherein the processing unit further includes:
a detection module for detecting the occurrence of a neuron spike in the received neuron electrical signals; and
a transmitter for transmitting data reflecting the occurrence of each detected neuron spike;
wherein the electrode is a part of an electrode array, the electrode array comprising:
a nonconductive layer of the flexible wiring circuit;
an array of electrodes, each electrode having a base section and a tip section, wherein the base section of each electrode is inserted into the nonconductive layer, such that the electrodes are held together by the nonconductive layer; and
an electrical connection located on the base section of each electrode to communicate with the respective electrode;
wherein the nonconductive layer rests on a platform portion of each electrode after the base section of each electrode is inserted into the nonconductive layer.

2. The system of claim 1, wherein a plurality of conductors are supported by the nonconductive layer for connection to respective ones of the plurality of electrodes, and wherein the nonconductive layer supports the plurality of electrodes.

3. The system of claim 1, wherein the nonconductive layer comprises an epoxy.

4. The system of claim 1, wherein the nonconductive layer comprises glass.

5. The system of claim 1, wherein the nonconductive layer comprises a flexible material.

6. The system of claim 5, wherein the flexible material comprises at least one of polyimide, parylene, and silicone.

7. The system of claim 1, wherein the electrodes are arranged in a two-dimensional matrix pattern.

8. The system of claim 1, wherein the electrodes are arranged in a honeycomb-like hexagonal pattern.

9. The system of claim 1, wherein the distances between neighboring electrodes varies.

10. The system of claim 1, wherein the electrodes increase in length from one side of the array to another side of the array.

11. The system of claim 1, wherein the plurality of electrodes have varying lengths.

12. The system of claim 11, wherein a first electrode has a length different that than of its immediately neighboring electrodes.

13. The system of claim 11, wherein the lengths of the plurality of electrodes are random.

14. The system of claim 1, wherein the plurality of electrodes have varying widths.

15. The system of claim 14, wherein a first electrode has a width different than that of each of its immediately neighboring electrodes.

16. The system of claim 1, wherein the width of the electrode is enlarged at or near the platform portion.

17. The system of claim 1, wherein the electrodes may apply an electrical stimulation signal.

18. The system of claim 1, wherein the electrodes may detect an electrical signal.

19. A brain implant system comprising:
   an electrode configured to be inserted in a brain and for sensing electrical signals generated by brain neurons;
   a flexible wiring circuit connected to the electrode and adapted to receive the neuron electrical signals sensed by the electrode;
   a processing unit for receiving the neuron electrical signals from the flexible wiring circuit, wherein the processing unit further includes:
      a detection module for detecting the occurrence of a neuron spike in the received neuron electrical signals; and
      a transmitter for transmitting data reflecting the occurrence of each detected neuron spike; and
   a buffer for storing digital neuron data before the detection module detects a neuron spike, and wherein contents of the buffer are overwritten when a spike is not detected.

20. The system of claim 19, wherein the detection module further includes:
   means for determining whether a received neuron electrical signal exceeds a threshold level; and
   means for detecting the occurrence of a neuron spike when the threshold level is exceeded.

21. The system of claim 19, wherein the electrode is part of an electrode array of a plurality of electrodes, the processing unit further includes:
   an analog-to-digital converter for converting neuron electrical signals, received from the plurality of electrodes, into digital neuron data and for multiplexing the digital neuron data; and
   a buffer for storing the digital neuron data after the detection module detects a neuron spike.

22. The system of claim 19, wherein the transmitter is a wireless transmitter.

23. A method for operating a brain implant system, comprising:
   providing an electrode configured to be inserted in a brain and for sensing electrical signals generated by brain neurons;
   receiving the neuron electrical signals sensed by the electrode over a flexible wiring;
   receiving the neuron electrical signals from the flexible wiring and detecting the occurrence of a neuron spike in the received neuron electrical signals;
   transmitting data reflecting the occurrence of each detected neuron spike;
   storing digital neuron data in a buffer before the neuron spike is detected; and
   overwriting contents of the buffer when a spike is not detected.

24. The method of claim 23, wherein the step of detecting the occurrence of a neuron spike further includes:
   determining whether a received neuron electrical signal exceeds a threshold level; and
   detecting the occurrence of a neuron spike when the threshold level is exceeded.

25. The method of claim 23, wherein the electrode is part of an electrode array of a plurality of electrodes, and wherein the step of receiving the neuron electrical signals from the flexible wiring further includes:
   converting neuron electrical signals, received from the plurality of electrodes, into digital neuron data and multiplexing the digital neuron data; and
   storing the digital neuron data after a neuron spike is detected.

26. The method of claim 23, further including:
   wirelessly transmitting the neuron spike data.

* * * * *

UNITED STATES PATENT AND TRADEMARK OFFICE
CERTIFICATE OF CORRECTION

| | |
|---|---|
| PATENT NO. | : 7,212,851 B2 |
| APPLICATION NO. | : 10/278853 |
| DATED | : May 1, 2007 |
| INVENTOR(S) | : John Philip Donoghue et al. |

It is certified that error appears in the above-identified patent and that said Letters Patent is hereby corrected as shown below:

In claim 9, column 13, line 4, "varies." should read --vary.--.

In claim 12, column 13, line 11, "that than" should read --than that--.

Signed and Sealed this

Third Day of July, 2007

JON W. DUDAS
*Director of the United States Patent and Trademark Office*

UNITED STATES PATENT AND TRADEMARK OFFICE
CERTIFICATE OF CORRECTION

PATENT NO. : 7,212,851 B2 Page 1 of 1
APPLICATION NO. : 10/278853
DATED : May 1, 2007
INVENTOR(S) : John Philip Donoghue et al.

It is certified that error appears in the above-identified patent and that said Letters Patent is hereby corrected as shown below:

On the Title Page, Section (73), add the following Assignee:

--Massachusetts Institute of Technology, Cambridge, MA (US)--.

Signed and Sealed this

Twenty Second Day of April, 2008

JON W. DUDAS
*Director of the United States Patent and Trademark Office*